(12) United States Patent
Shay et al.

(10) Patent No.: US 10,604,794 B2
(45) Date of Patent: Mar. 31, 2020

(54) METHOD TO MEASURE THE SHORTEST TELOMERES

(71) Applicant: The Board of Regents of The University of Texas System, Austin, TX (US)

(72) Inventors: Jerry W. Shay, Dallas, TX (US); Tsung-Po Lai, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 140 days.

(21) Appl. No.: 15/976,196

(22) Filed: May 10, 2018

(65) Prior Publication Data

US 2018/0340212 A1 Nov. 29, 2018

Related U.S. Application Data

(60) Provisional application No. 62/504,009, filed on May 10, 2017.

(51) Int. Cl.
| | | |
|---|---|---|
| *C12Q 1/683* | (2018.01) | |
| *C12Q 1/6855* | (2018.01) | |
| *C12Q 1/6858* | (2018.01) | |
| *C12Q 1/686* | (2018.01) | |
| *C12Q 1/6851* | (2018.01) | |
| *C12Q 1/6886* | (2018.01) | |
| *G16B 30/00* | (2019.01) | |

(52) U.S. Cl.
CPC ............. *C12Q 1/683* (2013.01); *C12Q 1/686* (2013.01); *C12Q 1/6851* (2013.01); *C12Q 1/6855* (2013.01); *C12Q 1/6858* (2013.01); *C12Q 1/6886* (2013.01); *G16B 30/00* (2019.02)

(58) Field of Classification Search
None
See application file for complete search history.

(56) References Cited

U.S. PATENT DOCUMENTS

2016/0032360 A1 2/2016 Keefe et al.
2016/0090630 A1 3/2016 Harley et al.

FOREIGN PATENT DOCUMENTS

EP 2907872 8/2015
WO WO 2016/059398 4/1916

OTHER PUBLICATIONS

Baird et al., "Extensive allelic variation and ultrashort telomeres in senescent human cells," *Nature Genetics*, 2003; 33: 203-7.
Bendix et al., "The load of short telomeres, estimated by a new method, Universal STELA, correlates with number of senescent cells," *Aging Cell*, 2010; 9: 383-397.
(Continued)

*Primary Examiner* — Young J Kim
(74) *Attorney, Agent, or Firm* — Norton Rose Fulbright US LLP

(57) ABSTRACT

The present disclosure encompasses methods and compositions for analyzing telomeres of genomic DNA, including the length of one or more telomeres. In specific embodiments, methods and compositions are employed for identification of the length of the shortest telomere in a collection of genomic DNA. In particular cases, the method greatly suppresses amplification of intra-genomic DNA fragments in comparison to telomeres by hindering their amplification using particular adaptors.

30 Claims, 11 Drawing Sheets
Specification includes a Sequence Listing.

(56) References Cited

OTHER PUBLICATIONS

Cheung et al., "Strain-specific telomere length revealed by single telomere length analysis in *Caenorhabditis elegans*," *Nucleic Acids Research*, 2004; 32(11): 3383-3391.
Holohan et al., "Perifosine as a potential novel anti-telomerase therapy," *Oncotarget*, 2015; 6(26): 21816-21826.
Holohan et al., "Telomeropathies: An emerging spectrum disorder," *J. Cell Biol.*, 2014; 205(3): 289-299.
Lai et al., "A method for measuring the distribution of the shortest telomeres in cells and tissues," *Nature Communications*, 2017; 8: 1356, 14 pp.
Lavrentieva et al., "High polymorphism level of genomic sequences flanking insertion sites of human endogenous retroviral terminal repeats," *FEBS Letters* 443, 1999; 341-347.
Sfeir et al., "Telomere-End Processing: The Terminal Nucleotides of Human Chromosomes," *Molecular Cell*, 2005; 18: 131-138.
Xing et al., "Constitutive Short Telomere Lenth of Chromosomes 17p and 12q but not 11q and 2p Is Associated with an Increased Risk for Esophageal Cancer," *Cancer Prev Res*, 2009; 2(5): 459-465.
Shay, Jerry. "Recent Advances in Telomeres and Telomerase in Relation to Aging and Cancer", *Tokyo Medical University, Institute of Medical Science, 1st International Symposium Role of Aging and Cancer*, Aug. 28, 2017.
Shay, Jerry. "Recent Advances in Human Telomere Biology as Related to Aging," *International Conference on Understanding Diversity in Telomere Dynamics*, Edinburgh, United Kingdom, 2016, Oct. 31, 2016.
Shay, Jerry. "TeSLA Detects the Shortest Telomere Shortening in Stimulated PBMCs Over Ten Days," *Telomeres and Telomerase, Cold Spring Harbor Laboratory*, May 2-6, 2017; Cold Spring Harbor, NY, May 2, 2017.

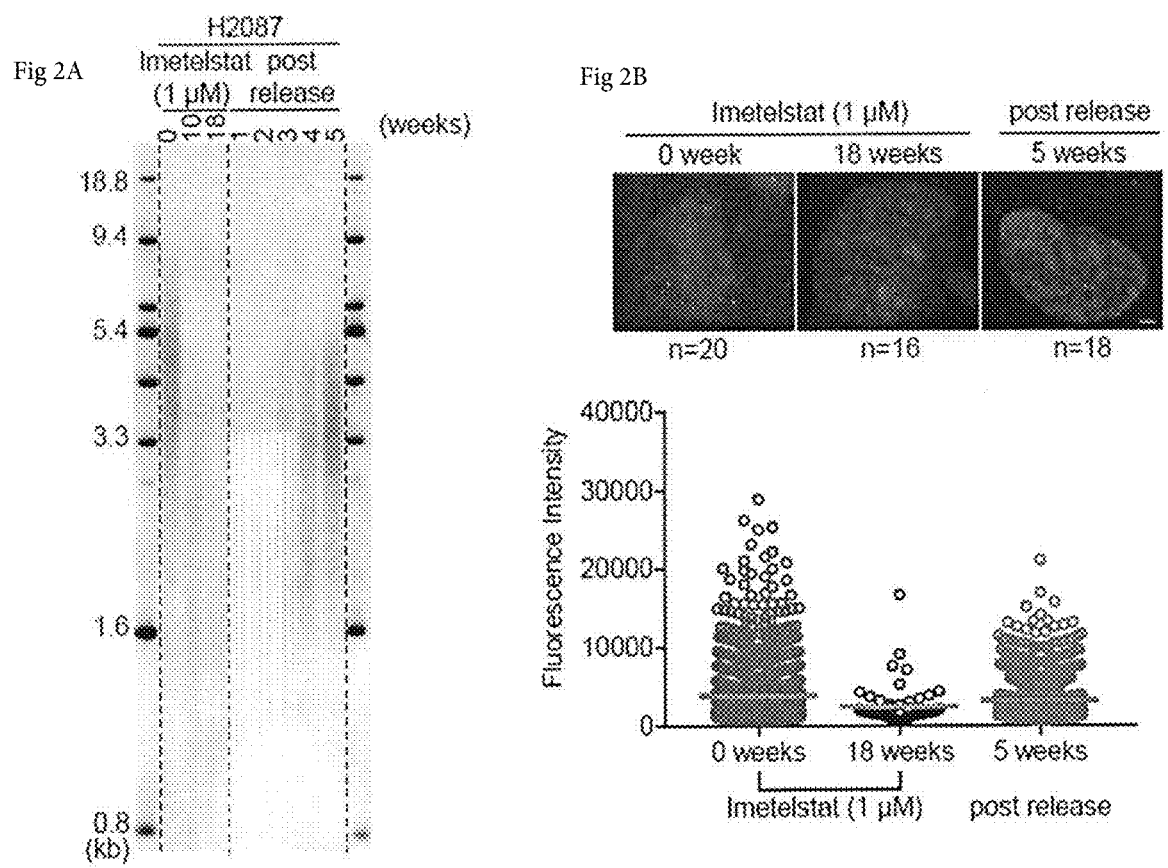
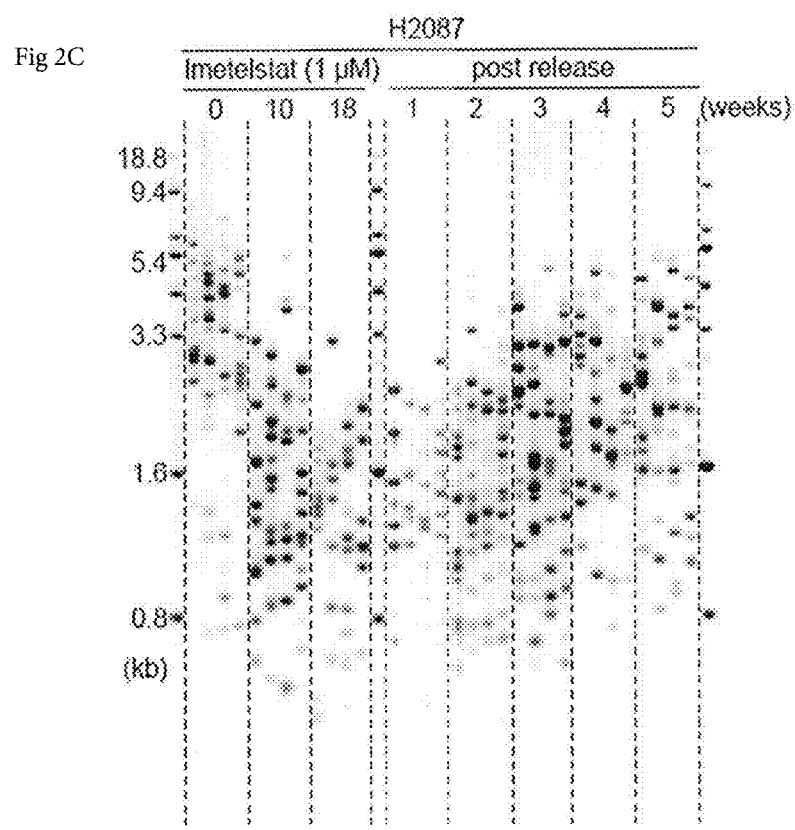

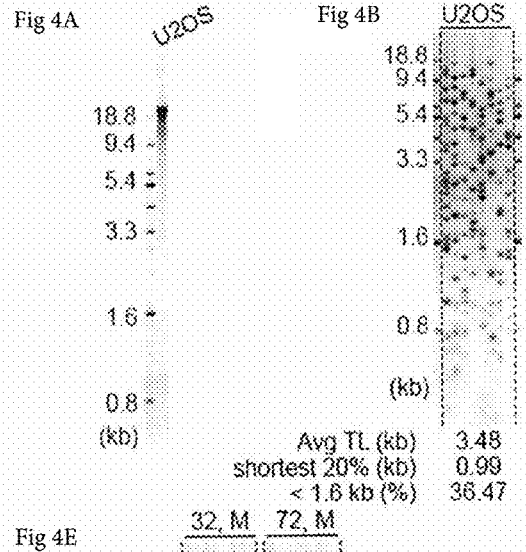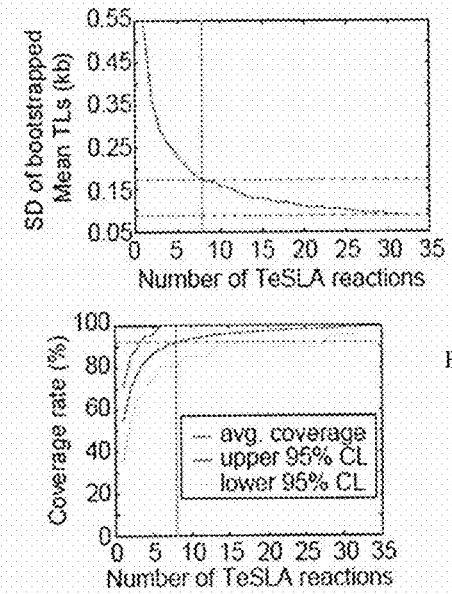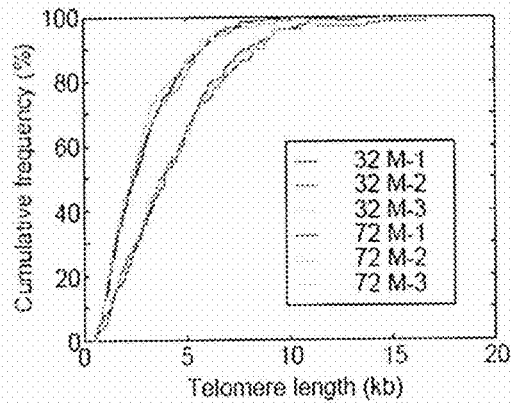

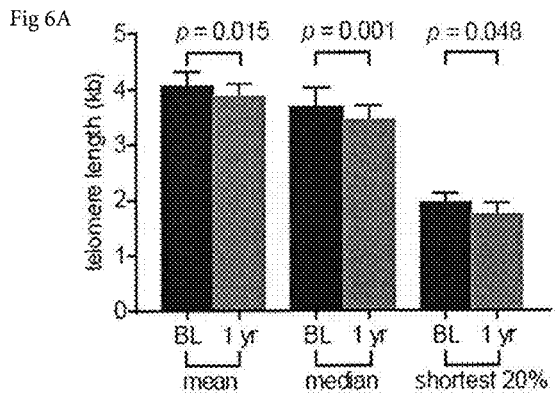
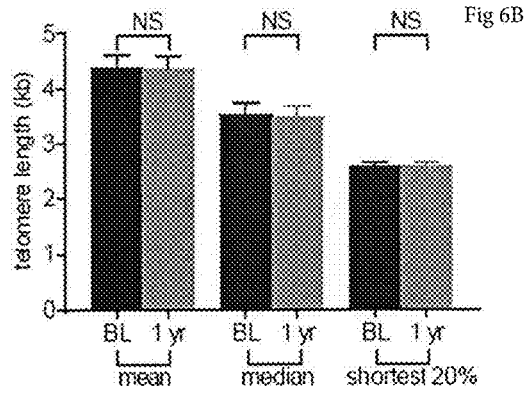
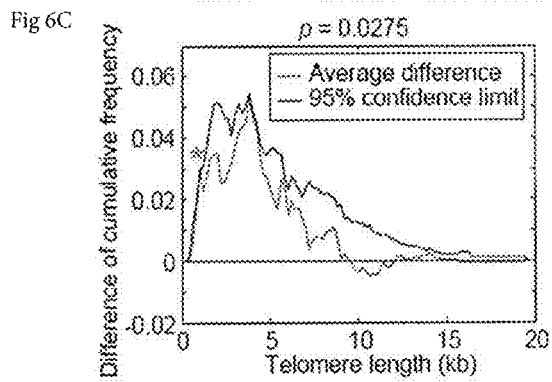
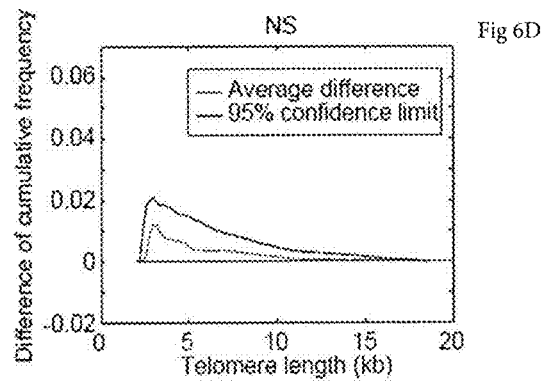
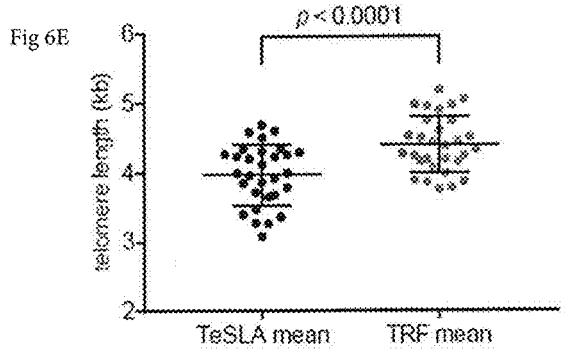
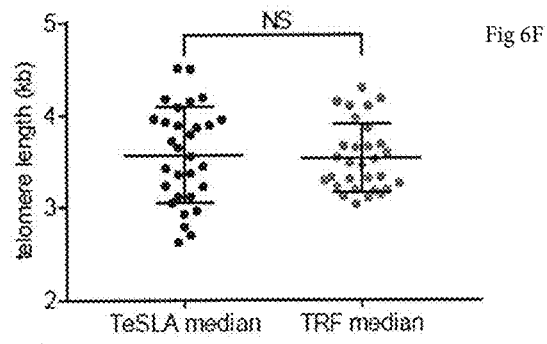
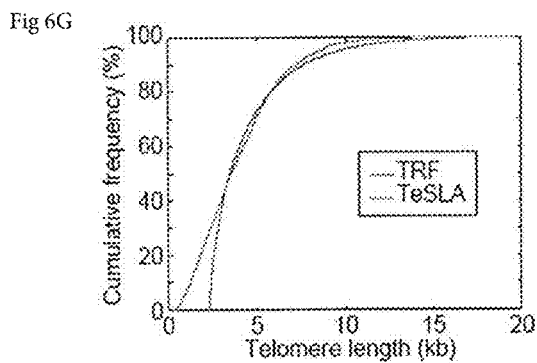
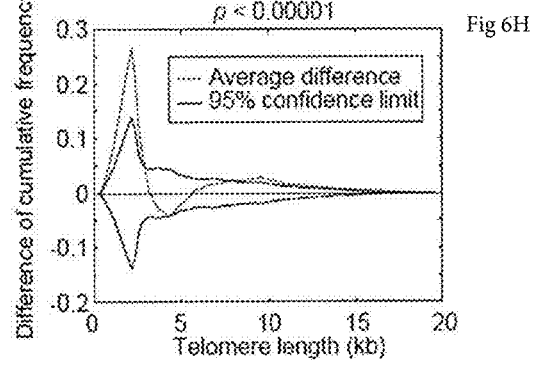

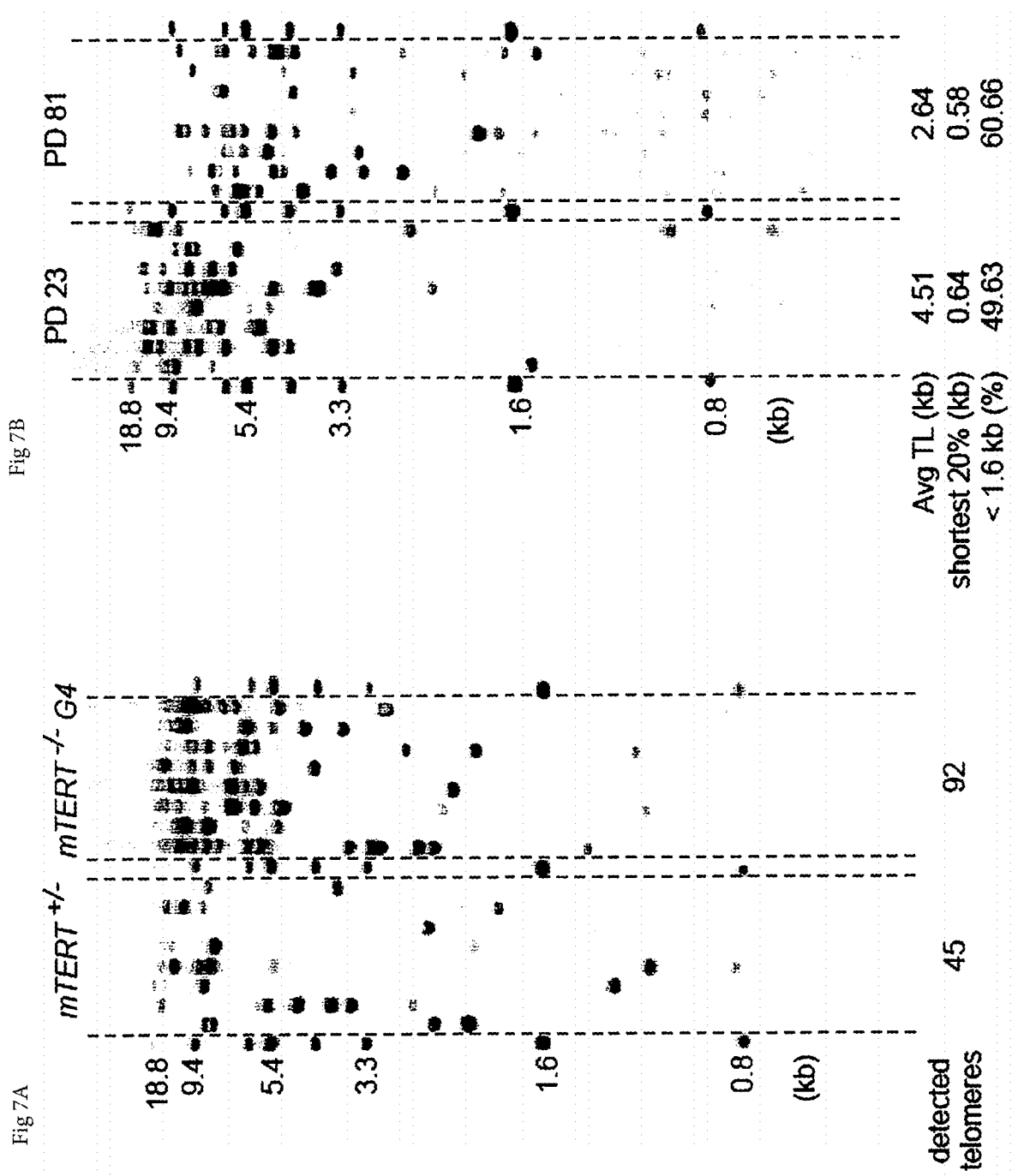

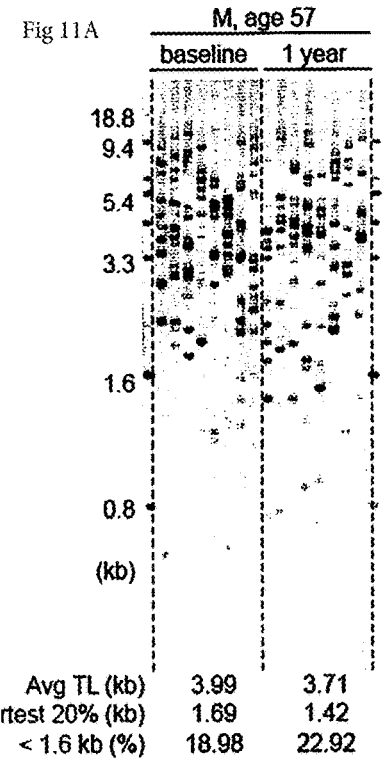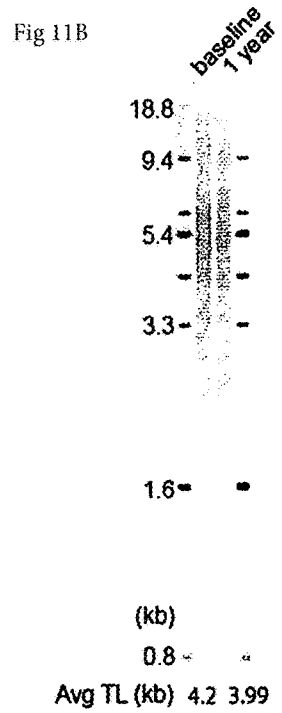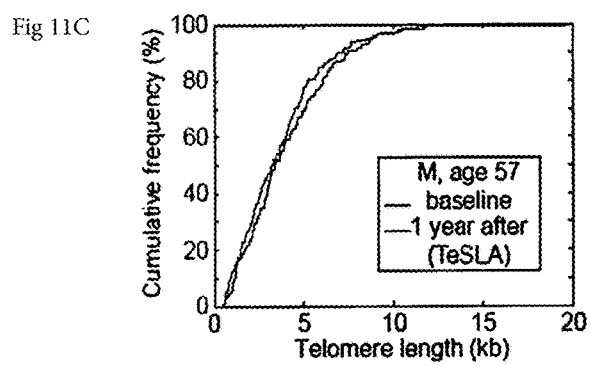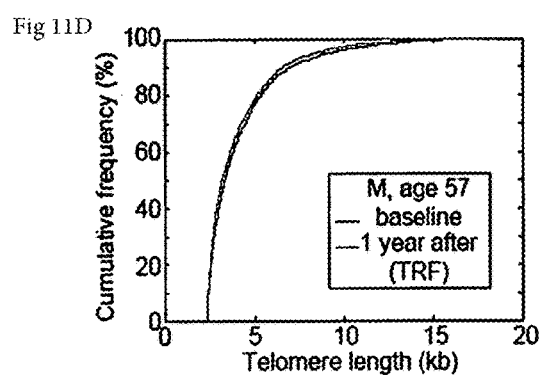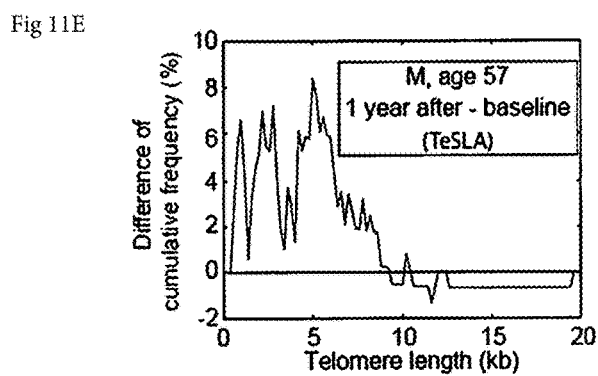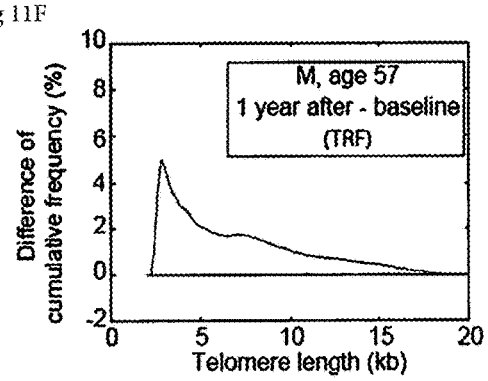

METHOD TO MEASURE THE SHORTEST TELOMERES

This application claims priority to U.S. Provisional Patent Application No. 62/504,009, filed May 10, 2018, which is incorporated by reference herein in its entirety.

TECHNICAL FIELD

Embodiments of the disclosure include at least the fields of cell biology, molecular biology, diagnostics, and medicine, including at least cancer medicine.

BACKGROUND

In vertebrates, telomeres consisting of repeat arrays of the canonical TTAGGG DNA sequence and their associated shelterin proteins reside at the ends of each chromosome to maintain genomic stability by preventing the ends from being recognized as DNA double strand breaks (Palm and de Lange, 2008). In most adult human somatic cells telomerase, a cellular reverse transcriptase that adds the repetitive DNA to telomeres is not detected. Therefore, telomeres progressively shorten with each cell division due to the "end replication problem" (Olovnikov, 1973; Watson, 1972). In humans, telomere shortening has been implicated as a risk factor for numerous diseases such as atherosclerosis, cancer, cardiovascular disease, diabetes mellitus, and liver cirrhosis (Fitzpatrick et al., 2007; Samani et al., 2001; Sampson et al., 2006; Shay, 2016; Wiemann et al., 2002). In addition, genetic diseases have been identified that have direct or indirect defects in the telomere maintenance machinery termed telomere spectrum disorders (or telomeropathies) (Holohan et al., 2014). Patients with these syndromes display accelerate telomere attrition and much shorter telomeres when compared with age-matched healthy controls (Armanios and Blackburn, 2012; Opresko and Shay, 2017).

Furthermore, it has been well demonstrated that it is the shortest telomeres, not average telomere length, that is able to activate the DNA-damage response and subsequently trigger an irreversible arrest of cell-cycle progression, cellular senescence (Fumagalli et al., 2012; Hemann et al., 2001; Herbig et al., 2004; von Zglinicki et al., 2005; Zou et al., 2004). Cellular senescence has been correlated with a variety of age-associated disease and may also serves as a potential tumor suppressor mechanism to protect genome integrity and prevent accumulation of oncogenic changes (Campisi, 2013). Furthermore, an increase in the percent of the shortest telomeres has been proposed to be a lifespan predictor in mammals (Vera et al., 2012). Thus, the load of the shortest telomeres may serve as a biomarker for telomere-associated aging disorders, including cancer.

Various methods have been developed for quantifying TL. Most of these analyses provide information on average TL (Montpetit et al., 2014; Nussey et al., 2014; Vera and Blasco, 2012). Southern blots of Terminal Restriction Fragment (TRF) analysis are considered to be the "gold standard" method for TL measurement by estimating the intensity and size distribution of the "telomeric smear" (Kimura et al., 2010). The TRF technique not only requires a large amount of genomic DNA, but due to the lower hybridization signal of the shortest telomeres, TRF underestimates information about the abundance of the shortest telomeres. The quantitative PCR (qPCR) TL measurement assay (Cawthon, 2002) has been widely used for high throughput (HT) testing to overcome the amount of the genomic DNA requirement for TRF and measures ratios of telomere signals to single copy gene signals. However, qPCR method only provides relative TL that is proportional to the average TL from a reference sample. In addition, the qPCR method is not suitable to quantify TL for cancer studies since most of cancer cells are aneuploidy (Holland and Cleveland, 2009).

Using live or fixed cells, TL can be measured by different Quantitative Fluorescence In Situ Hybridization (Q-FISH) methods. Although metaphase Q-FISH (Lansdorp et al., 1996) can detect TL from each chromosome, this method does not permit analyses on non-dividing cells, such as senescent cells or resting lymphocytes. Using resting or interphase cells Flow-FISH and HT Q-FISH are adapted for large scale studies to typically estimate mean TL of interphase cells. While these approaches are an improvement over Q-PCR, one disadvantage of these techniques is the probe not only binds to telomeric repeats but also interacts with non-specific components in the cytoplasm (Aubert et al., 2012; Wieser et al., 2006). HT Q-FISH is able to quantify each individual telomere signal in each nucleus, however, telomere clustering has been reported in lower eukaryotes (Gasser et al., 2004) and also in mammalian cells (Ramirez and Surralles, 2008). Therefore, the percentage of the shortest telomeres may be underestimated using HT Q-FISH. Importantly, probe hybridization kinetics does not permit robust quantitation of the shortest telomeres (<2-3 Kb).

Single telomere length analysis (STELA) (Baird et al., 2003) was designed to generate high resolution of TL measurements including the shortest telomeres on individual chromosomes. Using ligation and PCR based methods combined with Southern blot analysis STELA is able to provide detailed information about the abundance of the shortest telomeres but only on a specific subset of chromosome ends. This is one major limitation of STELA. The Universal STELA (U-STELA) (Bendix et al., 2010) method was reported to detect telomeres from each chromosome using a suppression PCR strategy to prevent the amplification of the intra-genomic DNA fragments. However, this suppression PCR method was designed for DNA with low molecular weight (less than 500 bp) (Lavrentieva et al., 1999). It is not sufficient to suppress the amplification of larger genomic DNA fragments. In addition, U-STELA is not efficient to detect TL over 8 kb (Bendix et al., 2010) which could affect the detection of accuracy of TL distribution. Finally, U-STELA detects interstitial telomeric repeats and thus affecting the accuracy of TL distributions.

The present disclosure provides methods and compositions to accurately detect the shortest telomeres among a plurality of telomeres.

BRIEF SUMMARY

Embodiments of the disclosure include methods and compositions for analyzing at least one telomere. In particular embodiments the methods and compositions allow analysis of more than one telomere, including some or all of the telomeres of a genome of a eukaryotic organism, such as a mammalian genome. A plurality of telomeres to be analyzed for the shortest telomere(s) may be of any kind, but in specific cases the plurality comprises the genome of one or more cells. In embodiments, methods and compositions allow for determination of a shortest telomere among a plurality of telomeres, including a eukaryotic genome. The shortest telomere may be of any length. In particular embodiments, among a plurality of telomeres the length of the sole shortest telomere is determined, although the length of the second shortest telomere in the plurality, the third shortest telomere, the fourth shortest telomere, and so forth is determined in addition to the length of the sole shortest telomere being determined from the plurality, in at least some cases.

In particular embodiments, the methods include successive steps that intentionally render un-amplifiable (or poorly amplifiable) the non-telomeric and at least some sub-telomeric sequences of a genome, thereby allowing selective amplification of telomeric sequences. In embodiments, an oligonucleotide having a unique sequence is ligated to the 5'-end of the C-rich strand of a telomere. In specific embodiments, the oligonucleotide comprises a C-rich region complementary to the G-rich strand of a telomere and comprises a unique sequence that is 5' to the C-rich region and that is not complementary to the G-rich strand of a telomere.

The sub-telomeric and non-telomeric sequences (which may be referred to as genomic or chromosomal sequences) are digested with one or more restriction enzymes to produce fragments with overhangs, such as AT or TA overhangs, followed by dephosphorylation of the 5' ends of the fragments (whether telomeric or sub-telomeric or non-telomeric). Adapters are ligated to the digested ends of the fragments. In particular embodiments, each adapter has two strands of different length but that has complementary regions. In the adapter, a first strand comprises a 5' phosphorylated overhang and a 3' overhang that comprises a second unique sequence. In the adapter, a second strand that is shorter than the first strand comprises a means for blocking ligation at its 3' end.

Amplification occurs using a first primer that is identical or substantially identical to the unique sequence in the oligonucleotide and a second primer that binds to the unique sequence in the adaptor. Because the non-telomeric and most sub-telomeric sequences are unable to be amplified, the telomeric sequences are selectively amplified. In specific cases, the telomeres are non-linearly amplified. The length of the amplified telomeres is determined. In particular embodiments, the information about the length of the amplified telomere and/or the identity of the particular chromosome of the telomere is used for a variety of purposes, including for clinical and/or diagnostic applications for an individual. An understanding of when the shortest telomeres initiate the onset of disease would be of diagnostic value where earlier interventions could reduce the severity of disease or even reduce the probability of disease onset (such as in telomeropathies).

Herein, the inventors in particular describe a new method called Telomere Shortest Length Assay (TeSLA). This method allows more sensitivity, efficiency and specificity for TL detection when directly compared to other methods for TL measurement. The inventors, in specific cases, used TeSLA in combination with an image-processing program that can automatically measure TL after Southern blot analysis. They were thus able to detect telomere dynamics from less than 1 kb to ~18 kb, especially the shortest telomeres, in normal aging processes, cancer progression, and telomere-related disorders in humans. Also, the TeSLA method was applied to ALT (alternative lengthening of telomere) cell lines and different mammals such as mice and bowhead whales to demonstrate the utility of this improved technology.

In one embodiment, there is a method of determining the length of one or more telomere(s) in a collection of genomic DNA molecules comprising telomeres, comprising the steps of providing a collection of genomic DNA molecules comprising telomeres having a G-rich strand and a C-rich strand, wherein the genomic DNA molecules comprise sub-telomeric sequences that are adjacent to the telomeres and comprise genomic sequences that are adjacent to the sub-telomeric sequences; ligating an oligonucleotide to the 5'-end of the C-rich strand, wherein the oligonucleotide and comprises a C-rich region complementary to the G-rich strand, and wherein the oligonucleotide comprises a first unique sequence that is 5' to the C-rich region and that is not complementary to the G-rich strand; digesting the sub-telomeric and genomic sequences with one or more restriction enzymes to produce fragments with overhangs, wherein the fragments comprise genomic sequences or comprise both sub-telomeric and telomeric sequences; dephosphorylating the 5' ends of the fragments; ligating adapters to the digested ends of the fragments, wherein each adapter has two strands with complementary regions, wherein a first strand comprises a 5' phosphorylated overhang and a 3' overhang comprising a second unique sequence, and a second strand that is shorter than the first strand comprises a means for blocking ligation at its 3' end; and amplifying (such as non-linearly) the telomeres using a first primer that is identical to the first unique sequence in the oligonucleotide and a second primer that binds to the second unique sequence in the adapter, to produce amplified telomeres; and determining the length of the amplified telomeres. The first unique sequence may be between 20 and 25 nucleotides in length, and/or the second unique sequence may be between 30 and 36 nucleotides in length. In specific embodiments, complementary regions of the adapter are between 18 and 24 nucleotides in length. The primer that binds to the first unique sequence in the oligonucleotide may be between 18 and 22 nucleotides in length. The primer that binds to the second unique sequence in the adapter may be between 18 and 22 nucleotides in length. In specific cases, the means for blocking ligation at the 3' end of the strand with the 5' phosphorylated overhang is a C3 spacer or, a dideoxynucleotide. Any amplification may or may not be by polymerase chain reaction. In specific cases, an oligonucleotide lacks a 5' phosphoryl group. In at least some cases, the length of the shortest telomere in the collection of genomic DNA molecules is determined. The length of the shortest, second shortest, third shortest, fourth shortest, fifth shortest, and so forth may be determined.

In particular embodiments, the methods utilize genomic DNA, such as mammalian DNA, including from a human. The genomic DNA may or may not be from a diseased cell. The genomic DNA may be from a stem cell, or a cancer cell, including a cancer stem cell. The genomic DNA may be from one or more cells in a benign lesion or from an immune cell, such as a peripheral blood mononuclear cell, T cell, NK cell, NKT cell, or mixture thereof. In specific cases, the T cell, NK cell, or NKT cell comprises an engineered receptor, for example a chimeric antigen receptor.

In certain cases, the genomic DNA is from an individual that has a medical condition, is suspected of having a medical condition, or is at risk of having a medical condition, including a genetic disease. The medical condition may be cancer, atherosclerosis, cardiovascular disease, diabetes, mellitus, or liver cirrhosis. The medical condition may be a telomeropathy, such as idiopathic pulmonary fibrosis, interstitial lung disease, Dyskeratosis congenital, aplastic anemia, cryptic liver disease, Revesz syndrome, Coats Plus syndrome, or Hoyeraal-Hreidersson syndrome.

In particular embodiments of the method, the length and/or abundance of the amplified telomeres are identified and in at least some cases the amplified telomeres are quantified, such as by Droplet Digital polymerase chain reaction (DDPCR), or both. In particular embodiments, determination of the length of the telomeres provides a diagnosis and/or prognosis for an individual that has a medical condition, is suspected of having a medical condition, or is at risk of having a medical condition. In specific cases, cells of the type of cells that were analyzed for telomere length are to be used for therapy.

In some cases, the genomic DNA is from cells from an individual at different ages, and the different ages of the individual may be separated by one or more years (for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more years), including by one or more decades, such as 1, 2, 3, 4, 5, 6, 7, 8, 9, or 10 decades.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 2A-2C. Measuring TL in long-term telomerase inhibition with imetelstat (1 µM) treatment and after a removal of drug in H2087 cells. (2A) Isolated DNA from H2087 cells with 1 µM imetelstat treatment for 0, 10 and 18 weeks, and post released from 18 weeks for 1, 2, 3, 4, and 5 weeks was digested with the same REs for TeSLA (BfaI/CviAII/MseI/NdeI) and then separated with 0.7% agarose gel for TRF analysis. (2B) Interphase Q-FISH; cells from H2087 with 0, and 18 weeks 1 µM imetelstat treatment, and 5 weeks after drug removal were used to measure TL by Q-FISH. The results were quantified using TFL-Telo software (n: numbers of nuclei were quantified for each time point as indicated above). (2C) Results of TeSLA using DNA as indicated. Four TeSLA reactions (30 pg of each reaction) were performed for each DNA sample.

FIGS. 4A-4H. Assessment of different variations of TeSLA. (4A) Telomere lengths of U2OS (a telomerase negative ALT cell line) determined by TRF analysis using the same restriction enzyme combination as TeSLA. Almost no information is provided about the short telomeres. (4B) Representative TeSLA results of U2OS (30 pg for each TeSLA reaction, 8 reactions). (4C) Standard deviations of bootstrapped distributions of mean TLs computed from (4B) show the estimation accuracy achieved by using n ($1 \leq n \leq 32$) lanes to estimate the mean TL. (4D) Coverage rates estimated from 32 TeSLA reactions in (B) based on bootstrapping. When 8 reactions were randomly selected from the 32 reactions, 92% of all telomeres were detected with bin sizes 0.5 kb ranging from 0~10 kb. Red (yellow) line indicates upper (lower) 95% confidence bounds of the coverage rates. (4E) Representative TeSLA results of PBMCs from a young (age 32) and an old (age 72) individual. (4F) Empirical distribution functions of TL from TeSLA (4E) of the triplicate results (blue, red and yellow lines for age 32 male) and triplicate results of the 72 year old male (purple, green and sky blue lines) of TeSLA from (4E). (4G) TeSLA of human bronchial epithelial cells (HBECs), Calu 6 (lung cancer cell line) and mixed DNA (HBEC:Calu 6=1:1) using 30 pg of DNA for each TeSLA reaction. (4H) Estimated probability density functions of TL from TeSLA results of Calu 6 (blue), HBEC (orange) and mixed DNA (red). The reference line (green dashed) represents a theoretical density function of TeSLA results when HBEC:Calu 6=1:1.

FIGS. 6A-6H. TeSLA is sensitive enough to detect changes of TLs in a one year period of normal human aging (6A, 6B) Bar charts comparing TLs in PBMCs measured at baseline and in one year period by TeSLA (6A) and TRF analysis (6B). The mean, median and shortest 20% TLs of 15 normal healthy subjects (age from 51 to 69) were averaged. P-values from paired t-tests are shown as indicated above. NS: no significant. (6C, 6D) The average changes of TL distributions in PBMCs in a one year period of 15 subjects measured by TeSLA (6C) and TRF analysis (6D). One-year differences in cumulative frequencies from each subject were computed (see FIGS. 11E and 11F as examples). The average of one-year changes in TL distributions of 15 subjects are shown in red and one-sided 95% confidence limit (black) is derived from permutation. The asterisk: the value (~1 kb of TL) lies outside of 95% confidence limit which indicates the most significant effect on telomere shortening. (6E, 6F) Scatter plots comparing TeSLA and TRF analysis for mean (6E) and median (6F) TL measurements (n=30) in PBMCs. (6G) Comparison of TeSLA and TRF analysis of empirical distribution curves of pooled TLs from all 30 DNA samples. (6H) The averaged differences (red) in cumulative frequencies (TeSLA-TRF) by the same method used in 6C and 6D show large difference between TeSLA and TRF in the short TL analyses (0.6~2.8 kb). Black lines are 95% confidence limits obtained from permutation.

FIGS. 7A-7B. TeSLA for telomere detections in mTERT knockout mice (G4) and lung fibroblasts from the bowhead whale. (7A) DNA extracted from mTERT$^{+/-}$ and mTERT$^{-/-}$ (4th generation, G4) mouse liver tissues were used to perform TeSLA (30 pg for each TeSLA reaction). Detected telomeres from mTERT$^{-/-}$ G4 (92 bands) are considerably more than telomeres that were detected from mTERT$^{+/-}$ liver tissue. (7B) TeSLA results of high quality DNA extracted from early (PD 23) and late (PD 81) passages of cultured bowhead whale lung fibroblasts. Both early and late passage cells contain a subset of the shortest telomeres that have not been identified by TRF analysis.

FIGS. 11A-11F. Using TeSLA and TRF analysis to determine changes of TLs for human longitudinally over a one year period. (11A, and 11B) TLs of DNA isolated from PBMCs from a healthy male at age 57 (baseline) and 1 year later were measured by TeSLA (11A) and TRF analysis (11B). (11C, and 11D) Empirical distribution curves based on TeSLA (11C) and TRF analysis (11D) results to represent TL distributions. The blue (red) lines are TL distributions at baseline (in 1 year after). The increase of cumulative frequency at a TL indicates the effect of TL shortening at the TL. (11E, 11F) One-year differences in cumulative frequencies as a function of TLs describe one-year change in TL distribution by TeSLA (11E) and TRF analysis (11F).

DETAILED DESCRIPTION

Figure 1A:
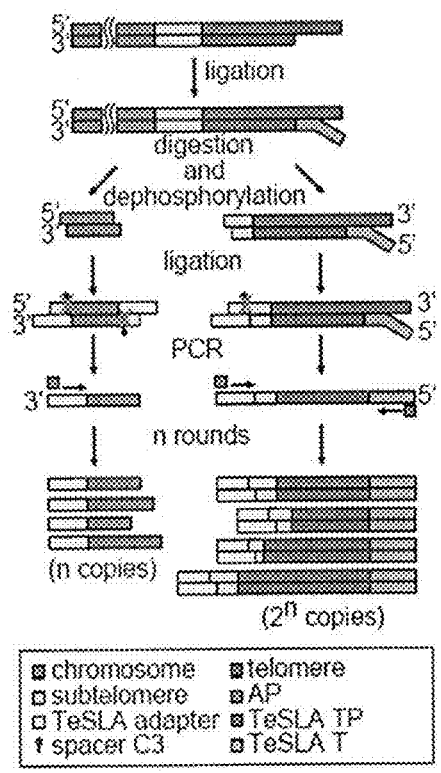
FIGS. 1A-1D. Overview of TeSLA (Telomere Shortest Length Assay) methods and comparison to Universal-STELA (U-STELA) and XpYp STELA. (1A) Schematic of overall TeSLA methods. (1B) 40 pg of DNA from RAJI cells was used in each U-STELA and TeSLA reaction to test specificity of primers for telomere amplification was tested as indicated (AP, adapter primer; U-TP, U-STELA teltail primer; T-TP, TeSLA teltail primer). (1C) The sensitivity of U-STELA and TeSLA was compared by serial dilution of input DNA from 5 to 40 pg. (1D) Using TeSLA (20 pg DNA for each reaction) and XpYp-STELA (250 pg and 500 pg of DNA for each reaction) to detect TL in BJ cells.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

Methods of the Disclosure

Embodiments of the disclosure include methods of analyzing the length of at least one telomere from genomic DNA. In particular cases, the methods effectively identify the lengths of all telomeres in a collection of telomeres, such as from genomic DNA from one or more cells. In particular embodiments, methods of the disclosure identify which telomere is the shortest or among the shortest in a plurality of telomeres. As an example, the methods identify which chromosome in genomic DNA from one or more cells has the shortest telomere among multiple (including all) telomeres from chromosomes of genomic DNA from the one or more cells. The identification of which telomere is shortest may be used as information upon which to take action, such as therapeutic or prognosis applications for an individual from which the genomic DNA was provided. In certain cases, the particular chromosome that has the shortest telomere provides information, whereas in additional or alternative cases a particular length of the shortest telomere provides information regardless of which chromosome it is. In some cases, when an individual has genomic DNA in which the shortest telomere has a length that is less than a certain value, then action may or may not be taken, such as preventative or therapeutic action or absence thereof. In specific embodiments, such a length is about 200-400 bp, although in alternative embodiments such a length is less or more. In other cases, when an individual has genomic DNA in which the shortest telomere has a length that is more than a certain value, then action may or may not be taken, such as preventative or therapeutic action or absence thereof.

Embodiments of the disclosure analyze telomeres from genomic DNA of an organism. Although any vertebrate organism having genomic DNA with telomeres may be included in the methods of the disclosure, in specific embodiments the genomic DNA is of a higher organism, including mammals, birds, and reptiles. In specific cases the methods pertain to mammals such as humans, horses, cows, dogs, cats, lamb, goats, rats, mice, bowhead whales, and so forth. The genomic DNA to be analyzed for its telomeres may or may not be obtained by the individual that performs the telomere analysis methods of the disclosure. In particular embodiments, the genomic DNA to be analyzed for its telomeres is processed (for example, to remove associated proteins) prior to the method, although in other cases it is not. Genomic DNA comprises telomere ends that have subtelomeric sequences adjacent to the telomeres, and then genomic sequences are adjacent to subtelomeric sequences and are present on the centromere side of the subtelomeric sequences.

Telomeres comprise two strands of DNA, one of which is G-rich and the other is C-rich, wherein the G-rich strand in nature has a 3' extension of G-rich sequence. In one step of the method, a sequence of which amplification would be utilized in subsequent method steps is added to the end of the telomeres furthest from the genomic DNA. Such a sequence may be added in any manner, but in specific embodiments an oligonucleotide is ligated to the 5' end of the C-rich strand. That oligonucleotide comprises sequence that is complementary to a region of the G-rich strand and comprises a unique sequence that is not complementary to the G-rich strand and will be targeted by a primer in subsequent steps of the method. The oligonucleotide lacks a 5' phosphoryl group, in particular embodiments. The oligonucleotide may be of any suitable length, but in specific cases it is in the range of a particular number of nucleotides in length. In specific embodiments, for each TeSLA telorette, the oligonucleotide comprises or consists of or consists essentially of 7 nt of C repeat (CCCTAA, for example) at the 3' end and then followed by 22 nt of DNA sequence, for example derived from MS2 phage. As long as each telorette has 7 nt of C repeat and then around 20 to 30 nt for PCR, then ligation and PCR may proceed. The sequence that is complementary between the oligonucleotide and the G-rich strand may be of any kind in length, although in certain embodiments it is in the range of 7 nt (or about 4-10 nt) of C rich repeat nucleotides in length. In specific cases, the oligonucleotide is a telorette, which as used herein is defined as an oligonucleotide that comprises multiple iterations of TTAGGG yet also comprises the unique sequence, and in specific cases the unique sequence is in the range of about 20-30 nucleotides in length. In particular embodiments, certain sequences in the unique sequence are avoided, such as telomere repeats (TTAGGG or CCCTAA). That is, the sequence of the unique sequence may be of any kind so long as it is not represented in the native genome of the individual in whose cells the telomeres are obtained, and in particular it is not C-rich such that it would anneal to the corresponding G-rich strand of the telomere.

In the next step, the genomic DNA is digested with one or more certain restriction enzymes that are able to cut in the subtelomeric region and/or the genomic sequences. In particular embodiments the one or more enzymes are not able to cut in the telomere sequences. In particular aspects the enzymes are not blunt cutters. In particular embodiments, digestion with the one or more enzymes leaves an overhang of 1, 2, 3, or 4 or more nucleotides. In specific cases the overhangs are 2 in length. The sequence of the overhang may be of any sequence, but in specific aspects the digestion generates TA and AT overhangs. In specific embodiments, the restriction enzyme has a recognition site that is 4 bases in length, although 5-base cutters or 6-base cutters may be used in alternative cases. In particular embodiments, the restriction enzyme is selected based upon the frequency and location of its recognition site. In certain aspects, the restriction enzymes are selected based on the frequency of AT/TA overhangs that they generate at the genomic and subtelomeric regions. In certain cases, a mixture of enzymes is utilized, one or more of which cuts in the subtelomeric region (such as at the telomere variant region) and at least one other that cuts universally in the genome. In specific cases, the restriction enzymes are BfaI, MseI, CviAII, and/or NdeI.

Following restriction digestion, the resultant fragments from the digestion are dephophorylated at their 5' end. However, in at least some cases the oligonucleotide that was ligated onto the 5'-end of the C-rich strand lacks a phosphoryl group on its 5' end. Dephosphorylation may occur by any standard means in the art.

In an adaptor ligation step, an adaptor is ligated to the ends of the fragments where appropriate. That is, an adaptor is ligated onto both ends of genomic fragments and fragments having entirely subtelomeric sequence. However, for the fragment that comprises the telomeres and a portion of subtelomeric sequence and for which the oligonucleotide is attached, the adaptor only ligates to the end of that fragment away from the telomere sequence. The adaptors are designed such that following their ligation to genomic fragments, the genomic fragments are prevented from amplifying in a $2^n$ manner, as with the case for the fragments with telomeres.

In particular embodiments, the adaptors have two strands A first strand of the adaptor comprises both a 5' overhang and a 3' overhang in relation to a second strand to which it has a complementary region. The 3' end of the first strand has a sequence that is unique to genomic sequences but that is also unique compared to the unique sequence of the oligonucleotide (the telorette). For the second strand, the 3' end is modified such that it cannot be ligated to another DNA molecule. In specific embodiments, the modification includes a C3 spacer, dideoxynucleotides, or both.

For the adapters, their length may be of a particular range. In particular cases, their length is sufficiently able to create a 5' TA or AT overhang in addition to approximately 20 nt that are complementary to the second strand, in addition to about 20-30 nt for adapter primer binding. In specific cases, the adapter comprises 5' AT or TA plus 20 nt that are complementary to the second strand, in addition to 11 nt that are random sequences for making a space between the primer binding site and second strand binding site, in addition to about 21 nt that are complementary to adapter primer (AP) plus 2 nt (for example, TT) that are random sequences at the 3' end. In a specific embodiment, the total length for the first strand is 56 nt long. The 3' overhang can be 25 to 35 nt long, for example.

Following adapter ligation, the fragments are subjected to PCR conditions, including using a first primer that is complementary to the first unique sequence in the oligonucleotide and a second primer that is complementary to the second unique sequence in the adapter. In specific cases, a PCR primer comprises the same sequence as the TeSLA telorette. In specific cases, only C-rich telomeric DNA is used for amplification. The PCR step produces amplified telomeres that may or may not be visualized and/or may or may not be quantified. In particular cases, the amplified telomeres are quantified by an automated device or method, and the quantification may be high throughput, such as using Droplet Digital polymerase chain reaction (DDPCR). In alternative methods, the amplified telomeres may be measured for length and/or intensity on a Southern blot.

Applications of Methods of the Disclosure

In humans, a range for the difference in length between the shortest and longest telomeres is generally between 0.5 kb and 15 kb. The present TeSLA methods can detect telomeres that are even shorter than 0.5 kb and up to 18 kb, and no other method is capable of doing this for all telomeres.

In certain embodiments, the methods of the disclosure are utilized for determining the risk for a disease. In the field it is well-established that the shortest telomeres, not average telomere length, is important in the onset of disease. Short telomeres can fuse to each other, leading to genomic instability at the next mitosis and increase the risk for disease such as cancer or telomeropathies. Therefore, the present methods are utilized to ascertain such a risk.

In embodiments of the disclosure, the methods of determining the length of the shortest telomere(s) in a genome are utilized for an intended purpose that may or may not be diagnostic and/or prognostic for an individual, for example. In particular cases, the length of the telomere is determined in order to ascertain a course of action. In some cases, the length of the telomere is determined to avoid a course of action. In certain cases, the length of the telomere is determined at one time point for an individual or at multiple time points for an individual.

In specific embodiments, a shortest telomere determination is undertaken for an individual to determine whether or not the individual should receive one or more therapies for any medical condition. In specific cases, an individual is tested for shortest telomere length to determine suitability for one or more therapies, including an approved therapy or a therapy provided in a clinical trial, for example.

In certain embodiments, an individual known to have or suspected of having or at risk of having a medical condition is subjected to a method of the disclosure. Although the medical condition may be of any kind, in specific embodiments the medical condition has short telomeres as a characteristic. In specific cases, the medical condition is a telomeropathy, such as idiopathic pulmonary fibrosis, interstitial lung disease, Dyskeratosis congenita, aplastic anemia, cryptic liver disease, Revesz syndrome, Coats Plus syndrome, or Hoyeraal-Hreidersson syndrome, for example.

In particular embodiments, the shortest telomere(s) is identified in an individual for the purpose of determining whether or not an individual has a medical condition or is at risk of having a medical condition. In some cases, having telomeres of a particular length identifies that an individual has or will have a particular medical condition, whereas in other cases having telomeres of a particular length identify that the individual will not have a particular medical condition. In certain cases, an individual is tested multiple times and over time the length of the shortest telomere is monitored. In some cases when the shortest telomere does not substantially shorten over time, then an individual has or will have or is at risk of having a particular medical condition, whereas in other cases when the shortest telomere does shorten over time, then an individual has or will have or is at risk of having a particular medical condition. Such analysis may or may not include one or more other analyses specific for the medical condition.

In specific cases, the method is utilized for analyzing the DNA of an individual, such as for commercial kits for DNA analysis for personal use.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

TeSLA: A Method for Measuring the Distribution of the Shortest Telomeres in Cells and Tissues Methods encompassed by the disclosure allow for more sensitive, efficient and specific for telomere length (TL) detection when directly compared to other methods for TL measurement. The methods may be used in combination with any other method, and in some cases may be used in combination with any imaging method, whether it is automated or not. As shown herein, one can detect telomere dynamics, especially for the shortest telomeres, in normal aging process, cancer, and telomere-related disorders in humans, for example. Also, one can apply the TeSLA method to different mammals such as mice, elephants, and bowhead whales to demonstrate the effectiveness of this improved technology.

Results

The Principle of TeSLA

A schematic presentation of the TeSLA method is shown in FIG. 1A. TeSLA is based on a ligation and PCR approach to detect amplified terminal restriction fragments which contain canonical telomeric repeats and subtelomeric regions from all chromosomes. In addition, TeSLA uses several new strategies to significantly improve the specificity and to intensify the sensitivity for TL measurements when compared to other methods.

For example, unlike U-STELA which ligates the terminal linker (telorette) to the 5' end of telomeric C-rich strand with restriction enzyme (RE) digested DNA that increase the possibility of ligation between subtelomeric sequences and digested genomic DNA fragments, the terminal linker ligation of the TeSLA method uses extracted genomic DNA (no RE digestion) with a mixture of newly designed terminal linkers (TeSLA-T 1-6; Table 1) to increase the specificity of single-stranded linkers to anneal and ligate to the 5' end at the telomeric C-rich strand. Each TeSLA-T contains 7 nucleotides of telomeric C-rich repeats at the 5' end which is complementary to the 3' G-rich overhang followed by a unique sequence derived from bacteriophage MS2 for PCR.

TABLE 1

Examples of Oligonucleotides

| Oligos for TeSLA | SEQ ID NO: | Sequence |
|---|---|---|
| TeSLA-T1 | 1 | 5'-ACT GGC CAC GTG TTT TGA TCG ACC CTA AC-3' |
| TeSLA-T2 | 2 | 5'-ACT GGC CAC GTG TTT TGA TCG ATA ACC CT-3' |

TABLE 1-continued

Examples of Oligonucleotides

| Oligos for TeSLA | SEQ ID NO: | Sequence |
|---|---|---|
| TeSLA-T3 | 3 | 5'-ACT GGC CAC GTG TTT TGA TCG ACC TAA CC-3' |
| TeSLA-T4 | 4 | 5'-ACT GGC CAC GTG TTT TGA TCG ACT AAC CC-3' |
| TeSLA-T5 | 5 | 5'-ACT GGC CAC GTG TTT TGA TCG AAA CCC TA-3' |
| TeSLA-T6 | 6 | 5'-ACT GGC CAC GTG TTT TGA TCG AAC CCT AA-3' |
| TeSLA adapter short | 7 | 5'-GGT TAC TTT GTA AGC CTG TC[SpcC3]-3' |
| TeSLA adapter TA | 8 | 5'-[Phos] TAG ACA GGC TTA CAA AGT AAC CAT GGT GGA GAA TTC TGT CGT CTT CAC GCT ACA TT [SpcC3]-3' |
| TeSLA adapter AT | 9 | 5'-[Phos] ATG ACA GGC TTA CAA AGT AAC CAT GGT GGA GAA TTC TGT CGT CTT CAC GCT ACA TT [SpcC3]-3' |
| AP | 10 | 5'-TGT AGC GTG AAG ACG ACA GAA-3' |
| TeSLA TP | 11 | 5'-TGG CCA CGT GTT TGA TCG A-3' | where [Phos] represents 5' phosphorylation; [SpcC3] represents C3 spacer

Figure 8A:
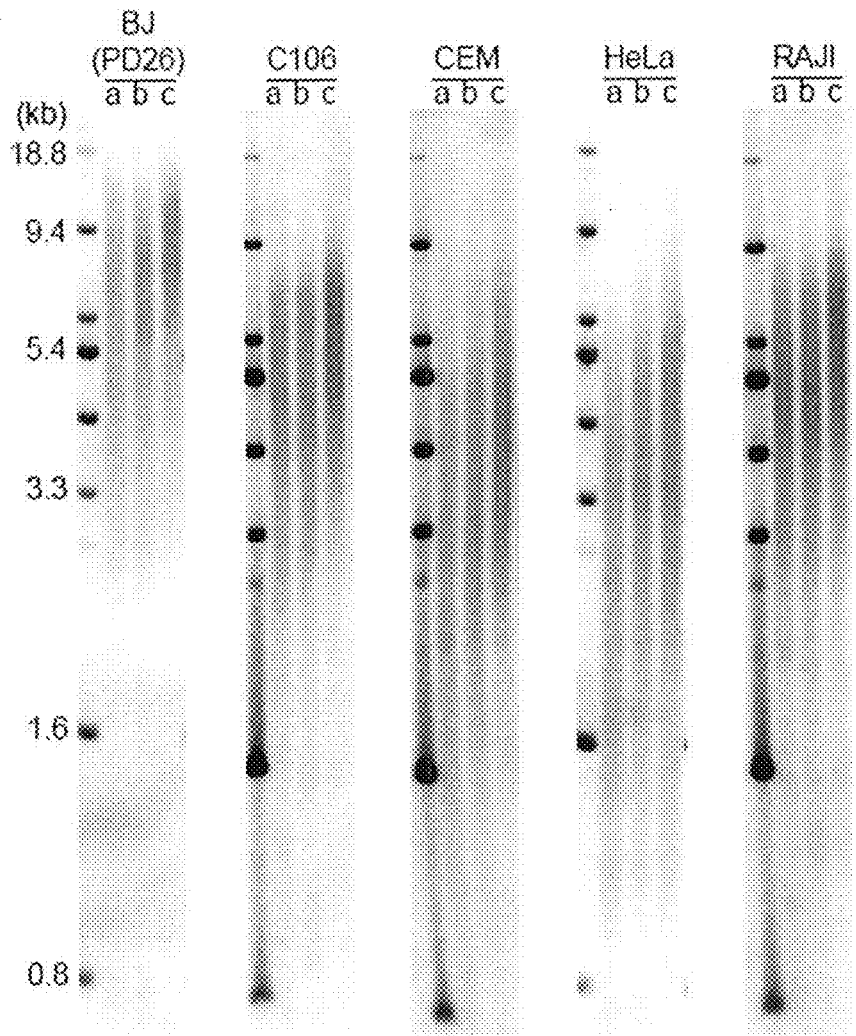
FIGS. 8A-8B. TRF analysis using different combinations of restriction enzymes. (8A) DNA of BJ, C106, CEM, HeLA, and RAJI cells were digested with (a) BfaI/CviAII/MseI/NdeI, (b) HphI/MnlI, and (c) AluI/HaeIII/HhaI/HinfI/MspI/RsaI. (8B) Quantification results of each cell line's TRF analysis in (8A).
Figure 8B:
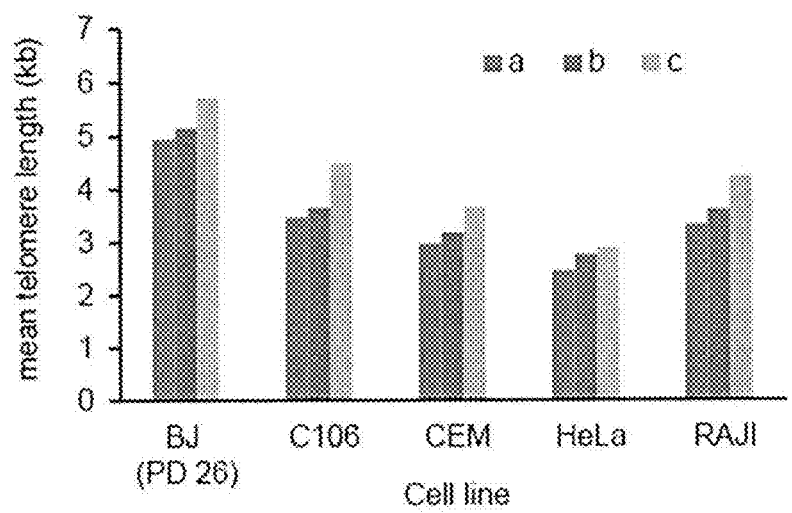

Second, since TeSLA is measuring telomeres from terminal restriction fragments, to minimize the measurement of subtelomeric regions that do not vary in length with cell replication and to create specific ends for ligation of linkers at the proximal ends of canonical telomeric repeats in TeSLA, the inventors chose a combination of four restriction enzymes (BfaI, CviAII, MseI, and NdeI) to digest TeSLA T-ligated genomic DNA and to create 5' TA and 5' AT overhangs for adapter ligation for the next step in the method. BfaI (which digests CTAG) and MseI (which digests TTAA) can digest DNA at telomere variant region that is adjacent to the canonical telomere repeats in subtelomeric regions (CTAGGG and TTAAGGG). CviAII (which digests CATG) and NdeI (which digests CATATG) can increase the frequency of generating 5' AT and 5' TA overhangs at genomic and subtelomeric regions. The inventors performed TRF analysis using genomic DNA from normal human fibroblasts (BJ) and different cancer cells (C106, CEM, HeLa, and RAJI) with the mixed panel of restriction enzymes for TeSLA or 2 additional different RE mixtures (AluI/HaeIII/HhaI/HinfI/MspI/RsaI and HphI/MnlI) that are able to significantly reduce the detection of subtelomeric regions by digesting DNA frequently at subtelomeric regions (Kimura et al., 2010; Steinert et al., 2004). The results demonstrated that the RE mixture for TeSLA further reduces detection of subtelomeric regions when compared to the other combinations of REs (FIGS. 8A and 8B). This also indicates that most RE cocktail mixtures may be overestimating even the average TL in cells. After enzyme digestion, the inventors performed 5' dephosphorylation using shrimp alkaline phosphatase to prevent ligation between the telomeric DNA fragments and the digested genomic DNA fragments by adding extra sequences to subtelomeric region during the next step of TeSLA.

Third, to increase the ligation efficiency and the specificity of PCR for telomeric DNA amplification, the inventors generated two double-stranded linkers (5' AT and 5' TA overhangs) to tag genomic and subtelomeric sequences (see material and methods; Table 1 and FIG. 1A). The adapters contain phosphorylated 5' AT or TA overhang and a C3 spacer at the 3' end followed by a unique 3' overhang being complementary to adapter primers for the subsequent PCRs. The adapters were designed to contain phosphorylated 5' AT or TA overhang and a C3 spacer at the 3' end followed by a unique 3' overhang being complementary to adapter primers to facilitate ligation to only occur between the 5' end of adapters and 3' end of genomic/telomeric C-rich DNA fragments.

Fourth, after adapter ligation, multiple PCR reactions are performed to amplify tagged telomeric DNA fragments while preventing amplification of tagged genomic DNA fragments by using a primer that is complementary to the adapter together with a downstream primer that is identical to the 5' tail of TeSLA-Ts. Because the C-rich telomeric DNA fragments are tagged with TeSLA-Ts and adapters on both ends, multiple copies of tagged telomeres can be amplified at each cycle of PCR. Since genomic DNA fragments are ligated only at the 5' end, the genomic DNA fragments can only be amplified one copy at each PCR cycle.

Figure 9A:
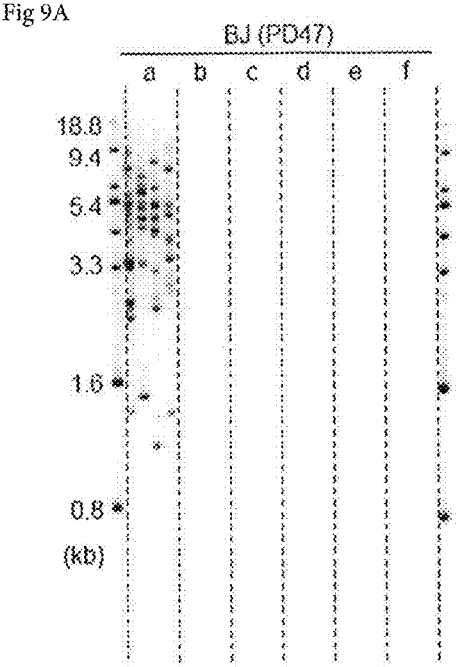
FIGS. 9A-9C. Validation of TeSLA. (9A) DNA from BJ cells was used to perform TeSLA; a, positive control; b, negative control without primers for PCR; c, no TeSLA-Ts for ligations at telomere overhangs; d, without digestion with restriction enzymes; e, no TeSLA adapters for ligations at genomic and subtelomeric DNA; f, no ligase for any ligation reactions. (9B) DNA from Jurkat cells with different viabilities was separated on 1% agarose gel to evaluate DNA integrity. (9C) TeSLA of Jurkat cells with different percent viable cells.
Figure 9B:
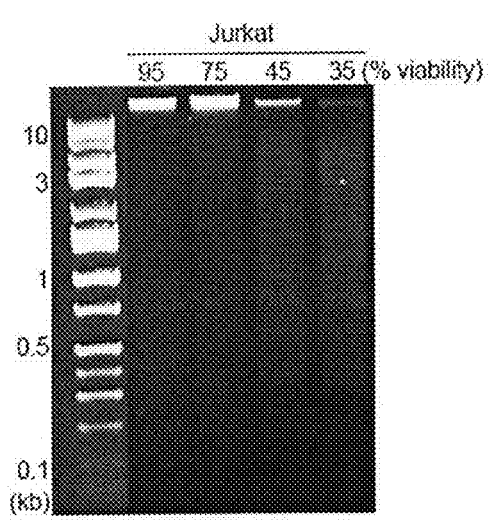
Figure 9C:
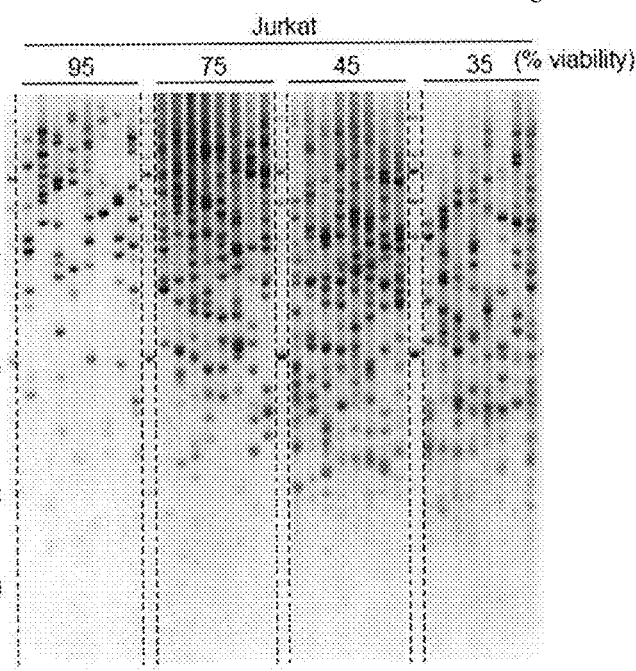

To validate the specificity of TeSLA for TL measurement, the inventors used genomic DNA from BJ human fibroblasts to perform TeSLA (FIG. 9A). In the absence of either TeSLA Ts, restriction enzyme digestion, adapters, or T4 DNA ligase, there are no telomere-specific products detected by a hypersensitive telomere specific probe (Lai et al., 2016). The inventors also determined the effect of DNA degradation on TeSLA for TL detection using human Jurkat suspension leukemic cells. To obtain Jurkat cells a variable percent of viable cells, the inventors reduced nutrients to Jurkat cells and allowed medium to become more acidic. The inventors then evaluated the integrity of DNA in Jurkat cells with different percent viable cells (95, 75, 45 and 35% viable) and then performed TeSLA. Cells with lower viability have more degraded DNA and more short telomeres that are detected by TeSLA (FIGS. 9B and 9C). Thus, DNA integrity is essential to obtain reliable results using TeSLA for TL measurement (or for that matter all telomere detection methods).

TeSLA Provides More Detailed Information of TL Compared to STELA and U-STELA

STELA, U-STELA and TeSLA are designed to analysis telomere dynamics especially the distribution of the shortest telomeres with limited starting material. Therefore, the inventors compared the sensitivity and specificity of TeSLA to U-STELA and XpYp STELA. In addition, to the canonical telomeric ends of chromosomes, short telomere repeats (between 2 to 25 repeats) called interstitial telomere sequences (ITSs) are present in numerous intra-chromosomal locations (Ruiz-Herrera et al., 2008). To preferentially amplify tagged telomeres, the U-STELA uses a "panhandle" design of the proximal linker to ligate both ends of genomic fragments to suppress subsequent PCR amplification (Bendix et al., 2010). However, this suppression PCR strategy is designed for low molecular weight products (Lavrentieva et al., 1999). Therefore this method will not completely suppress the amplification of genomic ITS DNA fragments that are potentially large.

Figure 1B:
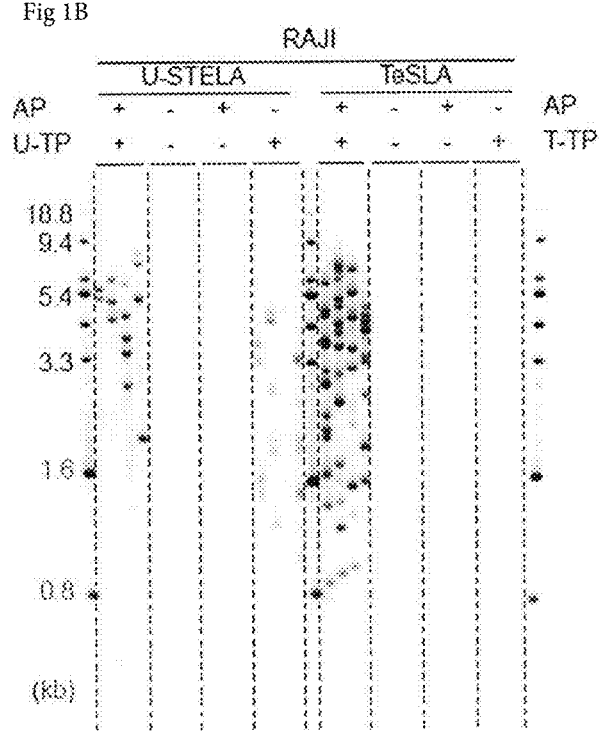

The inventors next compared the specificity of PCR amplification between U-STELA and TeSLA. In the absence of one or both primers, TeSLA does not have any detectable telomere products. However, there are several non-specific PCR products that can be observed after using only one of the primers to amplify the tagged DNA from U-STELA (FIG. 1B). These results document that the "panhandle" structure is not sufficient to suppress non-telomeric DNA amplification such as ITSs. In contrast, TeSLA is able to specifically detect chromosomal telomeric repeats without including genomic ITSs (FIG. 1B).

Figure 1C:
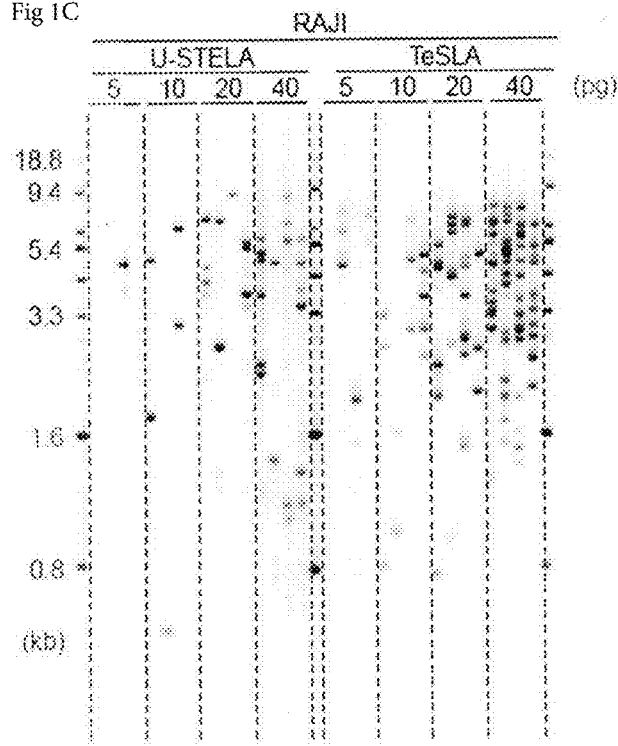

In addition, the inventors performed PCRs on serial dilutions of ligated DNA by TeSLA and U-STELA to compare the sensitivity of both methods for telomere detection. Using the same amount of input DNA, the inventors detected more telomere signals using TeSLA compared to U-STELA (FIG. 1C). This indicates that TeSLA is more sensitive and efficient compared to U-STELA for telomere detection.

Figure 1D:
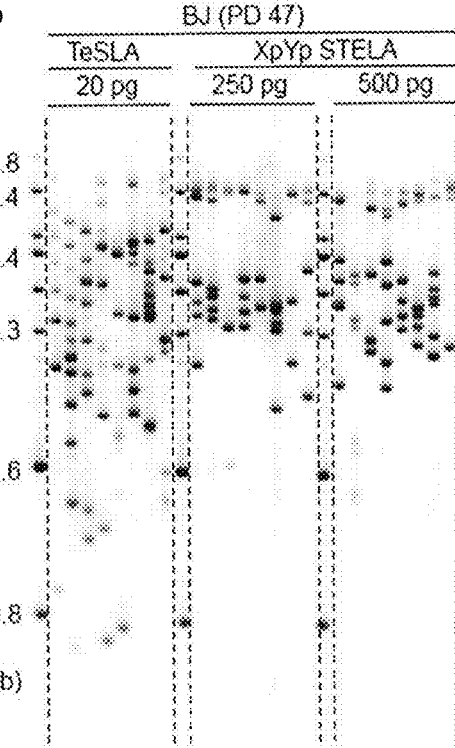

It is known that in a normal human cell each chromosome has different TLs (Lansdorp et al., 1996; Zou et al., 2004). Thus, the inventors directly compared the distribution of the telomere amplification products between TeSLA and XpYp STELA using the same BJ fibroblast DNA. The results show TeSLA is able to identify a wider distribution range of TL in comparison to XpYp STELA using considerably less input DNA (FIG. 1D). When comparing to XpYp STELA, TeSLA provides more precise information not only about the average TL but also about all the shortest telomeres, not just those of a specific chromosome end.

TeSLA is More Sensitive Compared to TRF and Q-FISH

To further examine the utility of TeSLA in studying telomere dynamics, the inventors evaluated TL dynamics in a telomerase positive non-small cell lung cancer (NSCLC) cell line (H2087). These cells were subjected to long-term telomerase inhibition treatment and then released to observe the dynamic of telomere re-elongation. The results were compared using TeSLA, TRF and telomere Q-FISH. Imetelstat is a lipid modified thio-phosphoramidate oligonucleotide that binds to the active site of telomerase RNA and thus robustly inhibits telomerase activity (Herbert et al., 2005). In a previous study (Frink et al., 2016) demonstrated that long-term imetelstat treatment shorten average TL in multiple NSCLC cell lines. In the present studies H2087 cells were continuously treated with 1 µM of imetelstat (3 times per week) for 18 weeks and then released from imetelstat treatment for 5 weeks. Cells were collected at 10 and 18 weeks with continuous imetelstat treatment and 1, 2, 3, 4, and 5 weeks after removal of imetelstat for TL measurement. Although the inventors are able to observe average TL shortening at 10, and 18 weeks treatment with TRF analyses, the relative intensity of shorter TL measurements as expected is significantly reduced (FIG. 2A). The inventors also examined TL using Q-FISH (using a PNA labeled telomeric repeat probe) with 0 weeks and 18 weeks of treatment, and 5 weeks in the absence of imetelstat (FIG. 2B). The inventors observed that only a few telomere signals with relatively low intensity were detected in H2087 cells with 18 weeks treatment compared to cells with 0 weeks treatment and 5 weeks after drug removal. Clearly these cells still have telomeric repeat at 18 weeks of telomerase inhibition, otherwise they would not have grown back upon release from imetelstat. This demonstrates that interphase Q-FISH is not sufficiently sensitive to measure TL for cells with extremely short telomeres (e.g. below 2-3 Kb). In contrast, TeSLA is able to detect TL in both imetelstat treated cells and cells post released from drug in a much more quantitative manner (FIG. 2C). Using TeSLA, the inventors were able to observe not only the average TL changes but also the changes in the distribution of the shortest telomeres from all chromosomes.

Software for TeSLA Quantification

Figure 3A:
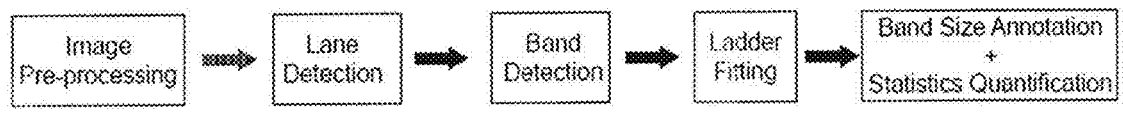
FIGS. 3A-3F. Overview of TeSLA image quantification software. (3A) The computational analysis pipeline automatically detects each telomere band location, then annotates the band sizes, and calculates the relevant statistics (e.g. average TL, the ratio of shortest TL, TL at 20 percentile, telomeres below 1.6 kb). (3B) Example of input TeSLA=image, tiff format recommended. The red frame indicates one lane detected by the software. At the ends of both sides of the image are the lane marker size standards (3C) Lane profile, generated by summarizing the pixel intensity values vertically from left to right. The red framed indicates one lane detected by the software. (3D) Band profile, generated for each lane by horizontally summarizing pixel intensity values. Each significant peak refers an individual band in that lane. (3E) Example of the final output. Red dots indicate individual bands. Green and magenta dots mark the overlapping bands that are counted twice or three times. Blue line crosses the 1.6 kb, which is the default threshold of calculating the shortest telomeres that other TL methods cannot detect. The software can calculate the ratio of TL below any given threshold. Magenta line indicates the TL size of the shortest 20% of telomeres. (3F) Histogram of TL distribution. There is a shift between samples with short and long telomeres.

In order to quantify the TeSLA images efficiently and accurately, the inventors developed user friendly software based on MATLAB programming, which allows for automatic detection and size annotation of telomere bands. The quantitation work flow is shown in FIG. 3A. The software is able to detect the center of each band, and annotate band size accordingly.

Figure 3B:
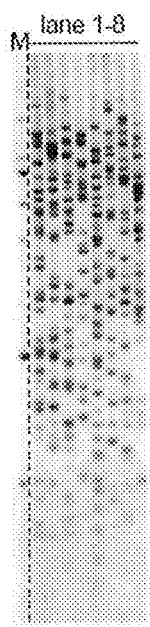
Figure 3C:
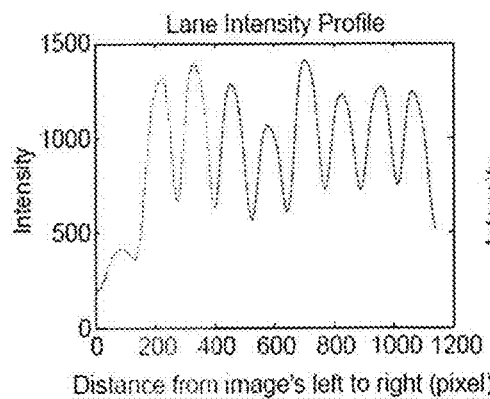
Figure 3D:
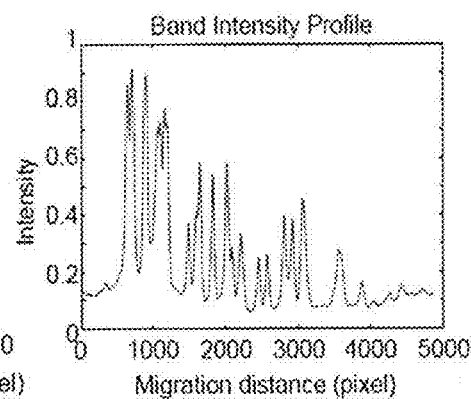

With the pre-processed image (FIG. 3B), the inventors first generate the lane profile by summarizing the normalized pixel intensity values along each vertical line from left to right (FIG. 3C). The software is then able to detect the center of each lane with watershed segmentation that determines significant peaks of the lane profile. Next, the software estimates the average lane width based on peak-to-peak intervals, and crops the regions of each individual lane for band detection (FIG. 3C). With each individual lane, the software plots the band profile by summarizing pixel intensity values horizontally from top to bottom and segments the significant peaks to indicate the centers of telomere bands (FIG. 3D) with user defined sensitivity level (default is 5). Band intensity is recorded by averaging the pixel intensity values among the local region of telomere bands. With the preliminary detection, the software displays all detected bands on its panel and gives the user the ability to adjust results by manually adding or deleting bands.

Figure 3E:
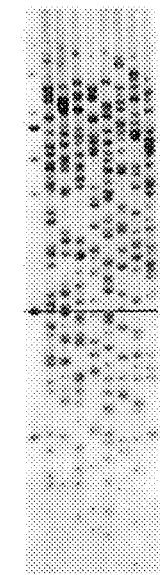
Figure 3F:
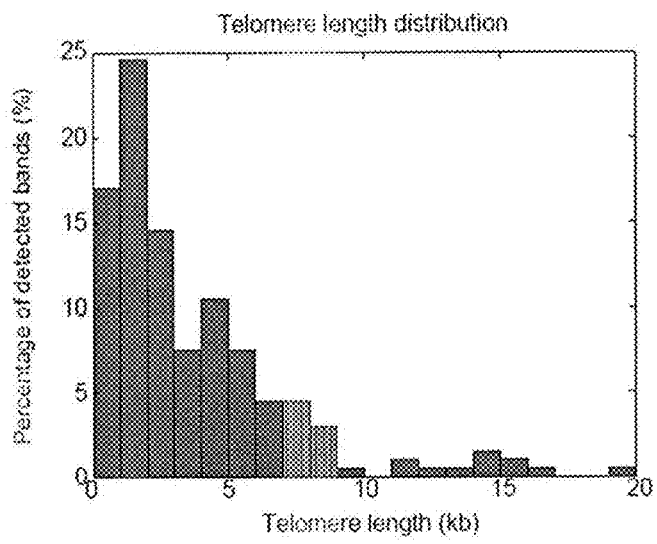

The software then fits the user defined ladder size standards at each region of the gel. The band size is then annotated and recorded by comparing each band, its pixel position, intensity value, and annotated size. When there are telomeres with similar sizes that cannot be separated well by electrophoresis, this results in more intense bands. However, the software is able to identify the potential overlapping bands and will compare the intensity of each band to other neighboring bands and will assign a double or triple count if the intensity value is two-fold more or even higher than the median intensity of the bands in the proximate neighborhood. Those bands with more than one count will be annotated with different colors in the final output (FIG. 3E). The telomere size distribution will be also plotted for each sample (FIG. 3F). Importantly, TeSLA detects the distribution of short telomeres (e.g. 0-3 kb) that is missed using other TL detection methods. With the annotated band sizes, the newly developed software rapidly calculates average telomere length, the percent of the shortest telomeres (with user defined threshold, default is 1.6 kb) and other relevant statistics.

TeSLA for TL Measurements

Since TeSLA measures TL using PCR to amplify tagged telomeres, the resolution of TL is limited by the efficiency and the length of amplicons for PCR amplification. To examine the upper size limit of TeSLA for TL measurement, the inventors applied TeSLA and TRF to evaluate TL of ALT cells (U2OS). Alternative lengthening of telomeres (ALT) is a telomerase independent mechanism that occurs in a small subset of cancers (Bryan et al., 1997). Lengths of telomeres in ALT cells are much longer and more heterogeneous than other cancer cells that are telomerase positive (Bryan et al., 1995). Using the same panel of restriction enzymes for TeSLA to perform TRF analysis, the inventors observed that the majority of telomeres distribute at higher molecular weight range (>18.8 kb) with a relatively small amount of telomeres at the lower molecular weight range (<18.8 kb) (FIG. 4A). Thus, TRF provides almost no information on the distribution of the shortest telomeres in ALT cells. Importantly, the inventors observed a wide range of telomere size distributions (from ~18 kb to below 0.8 kb) using TeSLA to measure TL of U2OS cells (FIG. 4B). The results not only demonstrate the heterogeneity of TL in ALT cells, but also show that the TL of ALT cells might be overestimated using TRF analysis. In addition, the upper limitation of telomere detection using TeSLA is at least 16 to 18 kb.

Figure 10A:
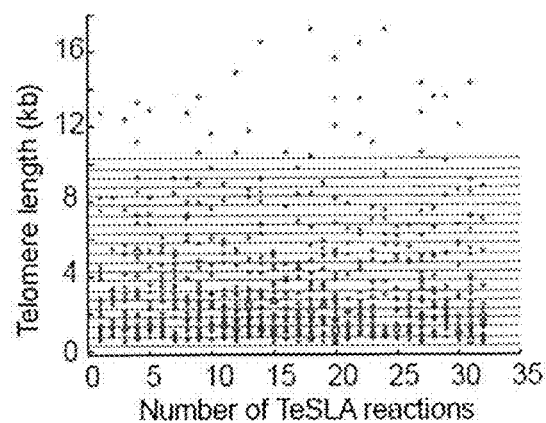
FIGS. 10A-10C. Intra-variation of TeSLA and TLs determined by TeSLA of BJ cells with different PDs. (10A) The scatter plot which represents distributions of TLs from TeSLA results (32 reactions) of U2OS cells shows heterogeneity of telomeres in ALT cells. (10B) Empirical distribution curves of quadruplets (8 TeSLA reaction of each) from TeSLA results for U2OS cells show no significant changes in each 8 TeSLA reaction. (10C) DNA extracted from different PDs (PD 26 and PD 49) of BJ cells were used to determine TL by TeSLA.
Figure 10B:
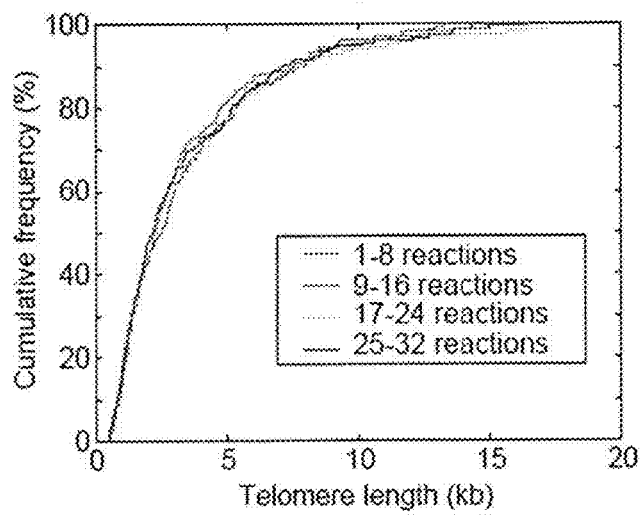

To achieve a proper representation of the shortest telomeres in a cell or population of cells, the inventors analyzed the molecular weight of each detected telomere from 32 TeSLA reactions of U2OS cells at the same time to determine the intra-variation of TeSLA. Since each reaction detects around 15-20 different molecular weights (FIG. 10A), the inventors determined the number of reactions that are necessary to obtain a reliable estimate of the entire distribution of various TLs in the U2OS cells. By using a bootstrapping method (see Methods), the inventors numerically simulated the estimation accuracy that would be achieved when "n" reactions ($1 \leq n \leq 32$) are employed to measure the TL distribution. The inventors used bootstrapping methods to compute the distribution of mean TLs and corresponding standard deviations (SDs) of the mean TLs at each number of reactions (FIG. 4C). The SD when using 8 reactions was 0.17 kb, which was about one-third of the SD when using one reaction. Since the gain in estimated accuracy is small with an additional 24 reactions, using 8 reactions is a reasonable number to estimate with confidence the population of detected telomeres. The inventors also computed coverage rates as a function of the number of reactions used. The results demonstrated that using 8 reactions was sufficient to cover 92% of the bins in a size range from 0-10 kb (FIG. 4D). Eight reactions were used as a unit to analyze the distributions of TL, which made the 32 reactions as four units. The TL distributions of quadruplicate runs did not show significant difference (FIG. 10B). This intra-assay coefficient of variation (%) of mean TL was 3.4. Although a previous study has evaluated telomere distribution of ALT cells using chromosome-specific STELA (Jeyapalan et al., 2008), TeSLA was more robust demonstrating the heterogeneity of telomeres in all chromosomes. Based on these intra-variation quantifications, the inventors use 8 TeSLA reactions for each sample to represent all following TL measurement.

To determine the inter-variation of TeSLA human PBMCs DNA donated by two healthy male donors (age 32 and 72 years old) were used to perform 3 independent TeSLA analyses on different days. PBMCs from the 32 year-old donor have considerably fewer of the shortest telomeres and longer average TL compared to the 72 year-old donor's leukocytes (FIG. 4E). Then, the inventors visualized the distribution of TL from each triplicate TeSLA result using empirical distribution curves (FIG. 4F). The inter-variation between the triplicates was small by visualization and the inter-assay coefficient of variations (%) of mean TL were: 1.6 for DNA from the 32 year-old donor and 3.9 for DNA from the 72 year-old donor.

It was next tested whether PCR amplification in the TeSLA method is biased toward amplifying the shortest telomeres. The inventors used extracted DNA from normal human bronchial epithelial cells (HBECs) at early passage (age 24, female) which have relatively long telomeres and a NSCLC cell line, Calu 6, which has very short telomeres (Frink et al., 2016) to perform TeSLA (FIG. 4G). After ligations, the same amount of ligated HBEC and Calu6 were mixed (HBEC:Calu 6=1:1) and used for PCR. If PCR in the TeSLA method was biased to amplify the shortest telomeres, the inventors expected the telomere distribution in the mixed DNA experiment would have more telomeres with short lengths and less telomeres with long length. The mean TL from the mixed DNA TeSLA (3.56 kb) is very close to the average of HBEC (4.97 kb) in combination with Calu 6 (2.04) results (FIG. 4G). The inventors further analyzed the distribution of TL from HBEC, Calu 6 and the DNA of the two cells mixed using a probability density function assay (FIG. 4H). The results show that the distribution of TL from mixed DNA is very similar to the distribution of TL from reference (HBEC:Calu 6=1:1) indicating that TeSLA PCR does not have a bias for over-amplifying the shortest telomeres.

Figure 10C:
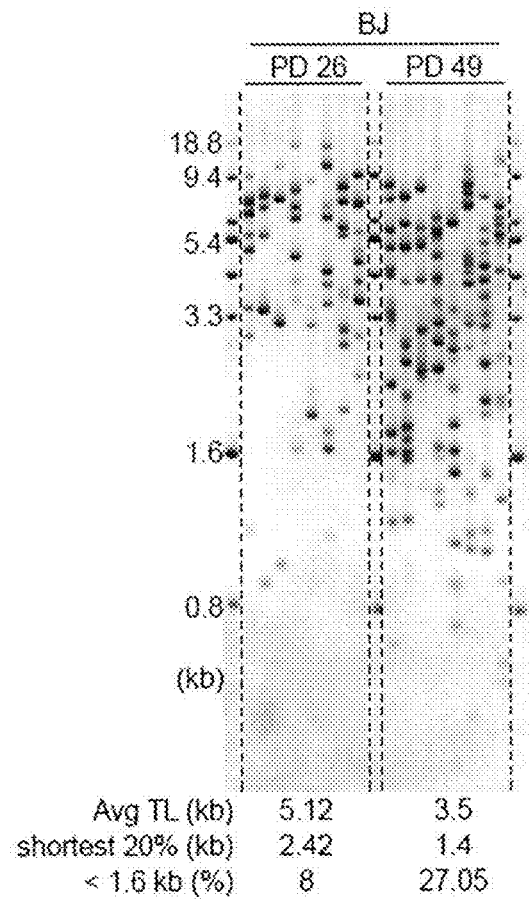

To evaluate whether 8 TeSLA reactions are sufficient to measure telomere shortening in vitro, the inventors used extracted DNA from two different BJ population doublings (PD) to perform TeSLA and then quantify TL from both samples (FIG. 10C). The results showed that telomere shortening is ~70 bp for each cell division, consistent with previous studies using chromosome-specific STELA and TRF analysis (Baird et al., 2003; Harley et al., 1990).

TeSLA Detects Changes of Telomere Dynamics of Colorectal Cancer Progression and Idiopathic Pulmonary Fibrosis (IPF)

Figure 5A:
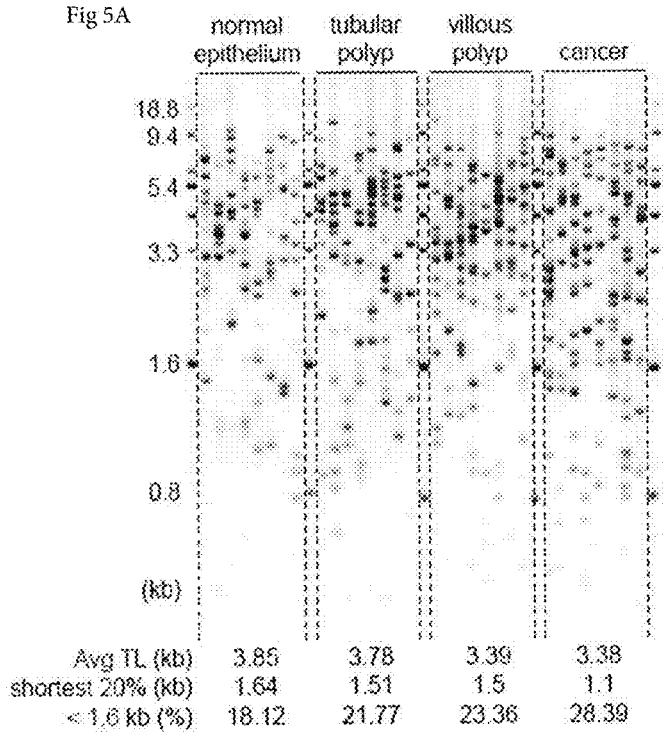
FIGS. 5A-5E. Using TeSLA to determine TL and distribution of telomeres in colon cancer progression and idiopathic pulmonary fibrosis IPF siblings compared to age match normal control. (5A) TeSLA results of normal colorectal epithelium, adenomas (tubular polyp and villous polyp) and colon cancer tissues from one colon cancer patient show shorter mean TL and increasing amount of the shortest telomeres in adenomas and cancer tissues compared to normal colorectal epithelium. (5B) Using TeSLA to determine TLs of DNA isolated from circulated leukocytes of the unrelated normal control, siblings with and without IPF. The age and gender are indicated above each TeSLA results. (5C, 5D, and 5E) Scatter plots of mean TL of TeSLA (C), the shortest 20% of telomeres (5D), and percent of the shortest TL (<1.6 kb) are shown for family members that have no IPF (3 unrelated controls and a family member without IPF) and 4 family members with IPF (5E).
Figure 5B:
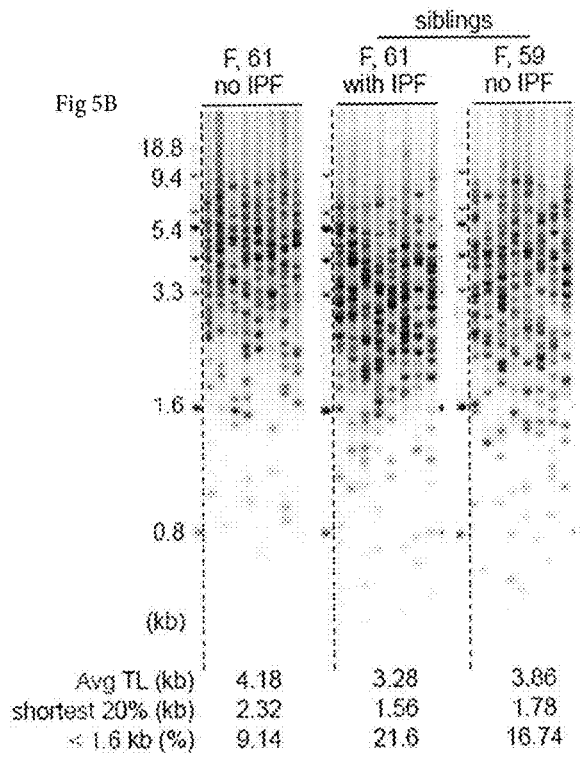
Figure 5C:
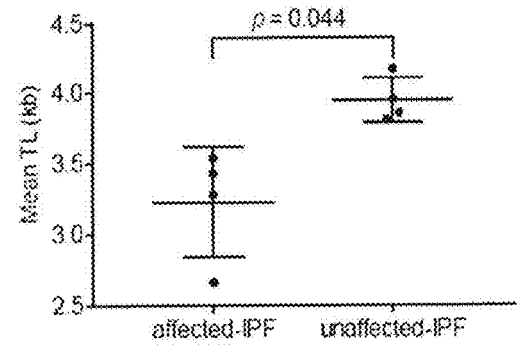
Figure 5D:
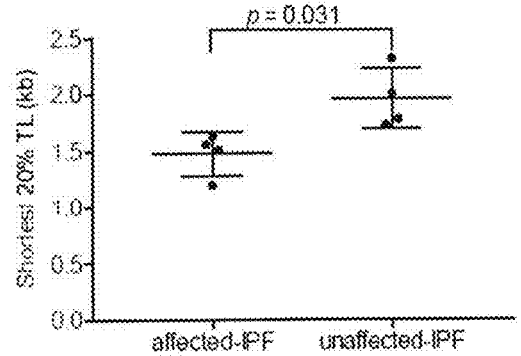
Figure 5E:
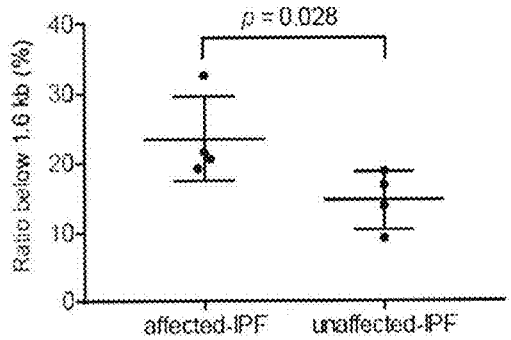

Short telomeres correlate with genetic alterations in cancer initiation (DePinho and Polyak, 2004). To investigate the relationship between cancer progression and telomere dynamics, the inventors performed TeSLA to measure TLs of normal colon epithelium, adenomas (villous and/or tubular polyps), and colorectal cancer tissues from a patient (Druliner et al., 2016). The inventors observed using TeSLA that DNA extracted from adenomas and cancer tissues have shorter mean TLs and more of the shortest telomeres below 1.6 kb compared to DNA isolated from normal colon tissue (FIG. 5A).

TRF, Q-FISH, and qPCR methods are widely used to assess TL to investigate telomere shortening in telomere spectrum disorders such as idiopathic pulmonary fibrosis, IPF (Armanios et al., 2007; Cronkhite et al., 2008; Diaz de Leon et al., 2010; Kropski et al., 2014; Parry et al., 2011; Tsakiri et al., 2007). TeSLA was used to examine leukocyte TLs from 8 probands (4 were affected and 4 were unaffected) of a familial kindred with IPF (unpublished). Affected family members have more short telomeres (below 1.6 kb) and shorter mean TL compared to unaffected family members (related and unrelated controls) (FIGS. 5B, 5C, 5D and 5E).

Taken together, while the TeSLA results of colon cancer progression and IPF development are consistent with previous studies measuring TL by other methods (Cronkhite et al., 2008; Diaz de Leon et al., 2010; Druliner et al., 2016; Stuart et al., 2015), TeSLA also provides more details about the distribution of telomeres and support that knowledge about the critically short telomeres may provide information about the stage when short telomeres contribute to cancer initiation and the onset of telomere spectrum disorders.

TeSLA is Sensitive Enough to Monitor Telomere Dynamics in Normal Human Aging Over a 1 Year Period Previous reports indicate that life stresses, infectious diseases, and inflammatory diseases can cause acute telomere shortening (Epel et al., 2004; Kotrschal et al., 2007; Pawelec et al., 2005; Vallejo et al., 2004). To directly compare telomere shortening effects detected by TeSLA and TRF analysis for normal human aging in a relatively short time period, the inventors used extracted DNA of PBMCs from healthy subjects who served as placebo treated volunteers in a clinical trial over a 1 year period (Salvador et al., 2016) to measure TLs by TeSLA and TRF analysis (FIGS. 11A, and 11B). After comparing changes of TL from each subject over a 1 year period (collected at baseline and 1 year), telomere dynamic changes in the placebo group (15 subjects; 8 females and 7 males, age 51 to 69) could be detected by TeSLA but not by TRF analysis (FIGS. 6A and 6B). TeSLA was able to detect changes in the mean, median, and 20th percentile TL by comparing TL at baseline to 1 year period.

To further understand the differences between TeSLA and TRF for PBMC TL measurements, empirical distribution curves were used to represent TL distribution measured by TeSLA and TRF analysis (FIGS. 11C and 11D) and then statistically tested changes of TL distribution of each subject in a 1 year time period by comparing differences of cumulative frequency of empirical distribution curves from each pair at baseline and 1 year after (FIGS. 11E and 11F). FIGS. 6C and 6D show the differences of cumulative frequencies averaged in the placebo group (15 pairs) from TeSLA and TRF analysis, which demonstrate that the effect of TL shortening is at relatively short telomeres (<6 kb) in both TeSLA and TRF analysis. Using a computed 95% confidence envelop curve by applying the permutation method to evaluate the significance of the observed difference curves from TeSLA and TRF analysis, the inventors found that data from TeSLA not only showed TLs decreased over 1 year period (one-sided P-value 0.0275) but also that the effect of telomere attrition was the most significant in the shortest telomeres (~1 kb) (FIG. 6C). In the TRF analysis (FIG. 6D), although the differences in cumulative frequencies still indicate the effect of TL shortening at short telomeres, the changes in TL distributions during 1 year was not significant (one-sided P-value 0.364), which is consistent with the results of mean, median and 20th percentile TLs (FIG. 6B).

Next, the TL distributions measured by TeSLA and TRF analysis were directly compared with all 30 DNA samples (15 pairs) in the placebo group. The mean TLs by TeSLA (average 3.97 kb) were consistently 10% shorter than the ones by TRF (average 4.40 kb) (FIG. 6E, paired t-test P-value<0.0001). However, the median TLs by TeSLA and TRF analysis were not statistically different (FIG. 6F, P-value 0.634). To compare and contrast differences of TeSLA and TRF measurements at the distribution level, the inventors visualized the empirical distribution curves from TeSLA and TRF analysis by integrating all 30 TL measurements. The results showed large discrepancies at the shortest telomeres while the differences of the two distribution curves were moderate at other TLs (FIG. 6G). By the averaged difference curves in cumulative frequencies (TeSLA-TRF) together with 95% confidence envelop curves, the inventors were able to estimate the difference of TeSLA and TRF analysis for detection of TLs in the placebo group (P-value<$10^{-5}$) (FIG. 6H) and observed that the difference between TL distributions by TeSLA and TRF analysis was dramatic in 0.6~2.8 kb ranges of sizes. However, the difference curve stayed within 95% confidence limits in the range of 3.0~7.8 kb indicating that TeSLA and TRF lead to consistent cumulative frequencies in the middle region and further explains why the median TLs by TeSLA and TRF were not significantly different (FIG. 6F). Thus, TeSLA is able to measure changes of PBMC TL over one year and uncovers distributions of shortest telomeres that have not been fully addressed by TRF analysis.

TeSLA can be Used in Studies of Model and Non-Model Organisms for TL Measurement The links between human diseases and TL have used tissue samples and cultured cells from human as well as laboratory mice. Previous studies demonstrated that progressive telomere shortening causes loss of tissue function in mTERT deficient mice. By Q-FISH analysis telomere attrition based only on fluorescence intensity indicated increasing amount of "telomere signal-free ends" in mTERT$^{-/-}$ mice at later generation (Erdmann et al., 2004; Meznikova et al., 2009). Most laboratory mice have many telomerase positive tissues with average TLs up to 40 kb (Lejnine et al., 1995) that is over the upper size limit (over 18 kb) by TeSLA for TL measurement. However, using TeSLA the inventors tested if they could uncover the proportion of the shortest telomeres in mice with TERT deficiency. With TeSLA, the inventors were able to detect increasing amounts of the shortest telomeres that are under 18 kb in the $4^{th}$ generation mTERT$^{-/-}$ mouse compared to mTERT$^{+/-}$ mouse in a C57BL/6 background using the same amount of input DNA (extracted from liver tissues; 30 pg per TeSLA reaction) (FIG. 7A). In the heterozygous mice most of the telomeres are not detected by TeSLA. However, in the mTERT knockout mice while more short telomeres are detected (FIG. 7A), the telomeres are not as short as observed in human cells with telomerase deficiencies. Going forward, other genetically engineering mouse models may provide information on the role of short telomeres in various pathologies Genome sequencing of the longest-living mammal, the bowhead whale, revealed that duplication and loss of genes related to DNA damage responses and repair may be involved in longevity and cancer resistance (Keane et al., 2015). The mean TL of cultured lung fibroblast cells from the bowhead whale is less than 10 kb by TRF analysis (Gomes et al., 2011). To examine the telomere dynamics of the bowhead whale in vitro by TeSLA, the inventors used DNA isolated from cultured lung fibroblast cells at different PDs. Even though the DNA from these cells was not degraded, the inventors found that a subset of very short telomeres (<1.6 kb) which has not been reported by TRF analysis can be detected in both early (PD 23) and late passage (PD 81) whale cells. There was telomere shortening and increasing amounts of the shortest telomeres at late passage (FIG. 7B).

Significance of Certain Embodiments

The majority of established methods for TL measurements are only useful for the detection of average TL. However, it is well established that the attrition of a single or a few shortest telomeres, not the average TL, triggers cellular senescence (Hermann, et al, 2001, Zou et al, 2004). Unlike methods that measure average telomere length, chromosome-specific STELA and U-STELA are capable of measuring at least some of the shortest telomeres. However, chromosome-specific STELA only can study telomeres from a few chromosomes and U-STELA is not sufficient to detect TL over 8 kb (Bendix et al., 2010) and detects non-specific signals that are likely to be interstitial telomere repeats (FIG. 1). In the present disclosure, using several new strategies to improve the ligation and amplification of telomeres, the inventors developed TeSLA that is capable of determining TLs from all chromosomes and to monitor the changes and distribution of the shortest telomeres, the average telomere length, as well as telomere lengths up to 18 kb. By directly comparing TeSLA to U-STELA and XpYp STELA for TL measurements (FIG. 1), the inventors demonstrated that TeSLA is more sensitive and specific for TL detection and generates more information of the spectrum of telomere distributions. The inventors also compared TeSLA to both TRF and Q-FISH methods for detecting extremely short telomeres after treating a NSCLC cell line with a telomerase inhibitor (Imetelstat) and then after Imetelstat was removed (FIG. 2). With TeSLA, but not TRF analysis and Q-FISH, the inventors were able to quantitate the length of the shortest telomeres using developed software to automatically quantify TeSLA results (FIG. 3).

TeSLA is Reliable for TL Measurement

The inventors were able to used extracted DNA from U2OS cells (a telomerase negative cell line having the ALT mechanism consisting of both very long and short telomeres) and different aged PBMCs from healthy donors to demonstrate TeSLA is a highly reproducible method for TL measurements (FIG. 4). Until the development of TeSLA that there was no technique that is capable of quantitating the entire spectrum of telomeres in ALT cells. However, the inventors were able to uncover heterogeneity of TLs in U2OS using TeSLA. The inventors determined that 8 TeSLA reactions containing 150-200 detected telomeres can cover >90% of telomeres that are shorter than 10 kb and could measure mean TL in a population of cells with a higher degree of confidence compared to other established methods. In addition, the inventors demonstrated that TeSLA can measure telomeres up to 18 kb which is sufficient to detect TL in almost all human normal somatic and cancer cells. Furthermore, the inventors demonstrated that TeSLA is not biased for amplifying the shortest telomeres that might affect the interpretation of the spectrum of telomeres in a population of cells.

Telomere Dynamics of Human Diseases and Aging

Critically short telomeres can lead to DNA damage responses and correlates with cancer progression, degenerative diseases and aging (Calado and Young, 2009; Kong et al., 2013; Opresko and Shay, 2017). To illustrate the changes of TL in human diseases that have been widely studied by other methods to measure mean TL, the inventors examined telomere dynamics in a colon cancer progression series and a familial kindred with IPF (FIG. 5). With TeSLA the inventors observed not only short mean TL but also increasing amounts of very short telomeres that correlate with cancer (>20% less than 1.6 kb) and IPF progression (>20% less than 1.6 kb). Going forward TeSLA may be a robust biomarker of clinical disease onset.

With TeSLA, but not TRF analysis, the inventors were able to detect changes in TL of PBMCs from healthy subjects over a 1 year period (FIG. 6). No other assay has demonstrated the ability to detect changes in TL in a one year period with small numbers of patient samples. Others have demonstrated the complexity of TLs measured in PBMCs by identifying variations in TLs and the rates of TL changes that are cell type-specific in vivo (Lin et al., 2016; Lin et al., 2015). Changes of mean TL that are measured by TRF analysis might not be detectable from a subset of cells with critically short telomeres in a mixed population PBMCs. TeSLA is very sensitive for detecting the shortest telomeres in a heterogeneous telomere background. Thus, TeSLA is capable of measure sub populations of cells in PBMCs, such as CD28− T cells, that have a lower capacity for cell division, shorter telomeres and high TL shortening rate compared to other sub types of cells in PBMCs (Weng et al., 2009). Thus, TeSLA may be able to identify critically short telomeres in specific immune cells that may be important in normal human aging. Using newly designed statistical analysis tools to compare TL distribution over a 1 year period, the inventors were able to determine the most dramatic effect on telomere shortening is on some of the shortest telomeres (around 1 kb in length) from a group of healthy human volunteers. This suggests the possibility that TeSLA, in combination with statistical analysis tools, could be used to detect pathological thresholds of disease at an earlier stage than have been previously available. Early diagnoses may result in the implementation of more effective interventions.

Telomere Dynamics in Other Animals

Besides studying changes of TLs in humans, TeSLA can be applied to evaluate the length of telomeres especially the shortest telomeres in other animals (FIG. 7). The inventors demonstrated that TeSLA is able to detect the distribution of the shortest telomeres in mTERT knockout mice. A recent study reported that telomere shortening is a critical factor for age-dependent cardiac disease in the NOTCH1 haploinsufficiency mouse model (Theodoris et al., 2017). Thus, TeSLA may serve as a powerful tool to study the relationship between changes of the shortest telomeres and age-dependent diseases in mouse models with deficiencies in telomere maintenance.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

The entire contents of all patents, published patent applications, and other references cited herein are hereby expressly incorporated herein in their entireties by reference.
1. Armanios, M., and Blackburn, E. H. (2012). The telomere syndromes. Nat Rev Genet 13, 693-704.
2. Armanios, M. Y., Chen, J. J., Cogan, J. D., Alder, J. K., Ingersoll, R. G., Markin, C., Lawson, W. E., Xie, M., Vulto, I., Phillips, J. A., 3rd, et al. (2007). Telomerase mutations in families with idiopathic pulmonary fibrosis. The New England journal of medicine 356, 1317-1326.

3. Aubert, G., Hills, M., and Lansdorp, P. M. (2012). Telomere length measurement-caveats and a critical assessment of the available technologies and tools. Mutat Res 730, 59-67.
4. Baird, D. M., Rowson, J., Wynford-Thomas, D., and Kipling, D. (2003). Extensive allelic variation and ultra-short telomeres in senescent human cells. Nature genetics 33, 203-207.
5. Bendix, L., Horn, P. B., Jensen, U. B., Rubelj, I., and Kolvraa, S. (2010). The load of short telomeres, estimated by a new method, Universal STELA, correlates with number of senescent cells. Aging Cell 9, 383-397.
6. Bryan, T. M., Englezou, A., Dalla-Pozza, L., Dunham, M. A., and Reddel, R. R. (1997). Evidence for an alternative mechanism for maintaining telomere length in human tumors and tumor-derived cell lines. Nat Med 3, 1271-1274.
7. Bryan, T. M., Englezou, A., Gupta, J., Bacchetti, S., and Reddel, R. R. (1995). Telomere elongation in immortal human cells without detectable telomerase activity. EMBO J 14, 4240-4248.
8. Calado, R. T., and Young, N. S. (2009). Telomere diseases. The New England journal of medicine 361, 2353-2365.
9. Campisi, J. (2013). Aging, cellular senescence, and cancer. Annu Rev Physiol 75, 685-705.
10. Cawthon, R. M. (2002). Telomere measurement by quantitative PCR. Nucleic Acids Res 30, e47.
11. Cronkhite, J. T., Xing, C., Raghu, G., Chin, K. M., Tones, F., Rosenblatt, R. L., and Garcia, C. K. (2008). Telomere shortening in familial and sporadic pulmonary fibrosis. Am J Respir Crit Care Med 178, 729-737.
12. DePinho, R. A., and Polyak, K. (2004). Cancer chromosomes in crisis. Nature genetics 36, 932-934.
13. Diaz de Leon, A., Cronkhite, J. T., Katzenstein, A. L., Godwin, J. D., Raghu, G., Glazer, C. S., Rosenblatt, R. L., Girod, C. E., Garrity, E. R., Xing, C., et al. (2010). Telomere lengths, pulmonary fibrosis and telomerase (TERT) mutations. PLoS One 5, e10680.
14. Druliner, B. R., Ruan, X., Johnson, R., Grill, D., O'Brien, D., Lai, T. P., Rashtak, S., Felmlee-Devine, D., Washechek-Aletto, J., Malykh, A., et al. (2016). Time Lapse to Colorectal Cancer: Telomere Dynamics Define the Malignant Potential of Polyps. Clin Transl Gastroenterol 7, e188.
15. Epel, E. S., Blackburn, E. H., Lin, J., Dhabhar, F. S., Adler, N. E., Morrow, J. D., and Cawthon, R. M. (2004). Accelerated telomere shortening in response to life stress. Proceedings of the National Academy of Sciences of the United States of America 101, 17312-17315.
16. Erdmann, N., Liu, Y., and Harrington, L. (2004). Distinct dosage requirements for the maintenance of long and short telomeres in mTert heterozygous mice. Proceedings of the National Academy of Sciences of the United States of America 101, 6080-6085.
17. Fitzpatrick, A. L., Kronmal, R. A., Gardner, J. P., Psaty, B. M., Jenny, N. S., Tracy, R. P., Walston, J., Kimura, M., and Aviv, A. (2007). Leukocyte telomere length and cardiovascular disease in the cardiovascular health study. Am J Epidemiol 165, 14-21.
18. Frink, R. E., Peyton, M., Schiller, J. H., Gazdar, A. F., Shay, J. W., and Minna, J. D. (2016). Telomerase inhibitor imetelstat has preclinical activity across the spectrum of non-small cell lung cancer oncogenotypes in a telomere length dependent manner. Oncotarget 7, 31639-31651.
19. Fumagalli, M., Rossiello, F., Clerici, M., Barozzi, S., Cittaro, D., Kaplunov, J. M., Bucci, G., Dobreva, M., Matti, V., Beausejour, C. M., et al. (2012). Telomeric DNA damage is irreparable and causes persistent DNA-damage-response activation. Nature cell biology 14, 355-365.
20. Gasser, S. M., Hediger, F., Taddei, A., Neumann, F. R., and Gartenberg, M. R. (2004). The function of telomere clustering in yeast: the circe effect. Cold Spring Harb Symp Quant Biol 69, 327-337.
21. Gomes, N. M., Ryder, O. A., Houck, M. L., Charter, S. J., Walker, W., Forsyth, N. R., Austad, S. N., Venditti, C., Pagel, M., Shay, J. W., et al. (2011). Comparative biology of mammalian telomeres: hypotheses on ancestral states and the roles of telomeres in longevity determination. Aging Cell 10, 761-768.
22. Harley, C. B., Futcher, A. B., and Greider, C. W. (1990). Telomeres shorten during ageing of human fibroblasts. Nature 345, 458-460.
23. Hemann, M. T., Strong, M. A., Hao, L. Y., and Greider, C. W. (2001). The shortest telomere, not average telomere length, is critical for cell viability and chromosome stability. Cell 107, 67-77.
24. Herbert, B. S., Gellert, G. C., Hochreiter, A., Pongracz, K., Wright, W. E., Zielinska, D., Chin, A. C., Harley, C. B., Shay, J. W., and Gryaznov, S. M. (2005). Lipid modification of GRN163, an N3'→P5' thio-phosphoramidate oligonucleotide, enhances the potency of telomerase inhibition. Oncogene 24, 5262-5268.
25. Herbig, U., Jobling, W. A., Chen, B. P., Chen, D. J., and Sedivy, J. M. (2004). Telomere shortening triggers senescence of human cells through a pathway involving ATM, p53, and p21(CIP1), but not p16(INK4a). Molecular cell 14, 501-513.
26. Holland, A. J., and Cleveland, D. W. (2009). Boveri revisited: chromosomal instability, aneuploidy and tum-origenesis. Nature reviews Molecular cell biology 10, 478-487.
27. Holohan, B., Wright, W. E., and Shay, J. W. (2014). Cell biology of disease: Telomeropathies: an emerging spectrum disorder. J Cell Biol 205, 289-299.
28. Jeyapalan, J. N., Mendez-Bermudez, A., Zaffaroni, N., Dubrova, Y. E., and Royle, N. J. (2008). Evidence for alternative lengthening of telomeres in liposarcomas in the absence of ALT-associated PML bodies. International journal of cancer Journal international du cancer 122, 2414-2421.
29. Keane, M., Semeiks, J., Webb, A. E., Li, Y. I., Quesada, V., Craig, T., Madsen, L. B., van Dam, S., Brawand, D., Marques, P. I., et al. (2015). Insights into the evolution of longevity from the bowhead whale genome. Cell Rep 10, 112-122.
30. Kimura, M., Stone, R. C., Hunt, S. C., Skurnick, J., Lu, X., Cao, X., Harley, C. B., and Aviv, A. (2010). Measurement of telomere length by the Southern blot analysis of terminal restriction fragment lengths. Nat Protoc 5, 1596-1607.
31. Kong, C. M., Lee, X. W., and Wang, X. (2013). Telomere shortening in human diseases. The FEBS journal 280, 3180-3193.
32. Kotrschal, A., Ilmonen, P., and Penn, D. J. (2007). Stress impacts telomere dynamics. Biol Lett 3, 128-130.
33. Kropski, J. A., Mitchell, D. B., Markin, C., Polosukhin, V. V., Choi, L., Johnson, J. E., Lawson, W. E., Phillips, J. A., Cogan, J. D., Blackwell, T. S., et al. (2014). A novel dyskerin (DKC1) mutation is associated with familial interstitial pneumonia. Chest 146, e1-7.
34. Lansdorp, P. M., Verwoerd, N. P., van de Rijke, F. M., Dragowska, V., Little, M. T., Dirks, R. W., Raap, A. K., and Tanke, H. J. (1996). Heterogeneity in telomere length of human chromosomes. Hum Mol Genet 5, 685-691.
35. Lavrentieva, I., Broude, N. E., Lebedev, Y., Gottesman, I I, Lukyanov, S. A., Smith, C. L., and Sverdlov, E. D. (1999). High polymorphism level of genomic sequences flanking insertion sites of human endogenous retroviral long terminal repeats. FEBS letters 443, 341-347.
36. Lejnine, S., Makarov, V. L., and Langmore, J. P. (1995). Conserved nucleoprotein structure at the ends of vertebrate and invertebrate chromosomes. Proceedings of the National Academy of Sciences of the United States of America 92, 2393-2397.
37. Lin, J., Cheon, J., Brown, R., Coccia, M., Puterman, E., Aschbacher, K., Sinclair, E., Epel, E., and Blackburn, E. H. (2016). Systematic and Cell Type-Specific Telomere Length Changes in Subsets of Lymphocytes. J Immunol Res 2016, 5371050.
38. Lin, Y., Damjanovic, A., Metter, E. J., Nguyen, H., Truong, T., Najarro, K., Morris, C., Longo, D. L., Zhan, M., Ferrucci, L., et al. (2015). Age-associated telomere attrition of lymphocytes in vivo is co-ordinated with changes in telomerase activity, composition of lymphocyte subsets and health conditions. Clin Sci (Lond) 128, 367-377.
39. Meznikova, M., Erdmann, N., Allsopp, R., and Harrington, L. A. (2009). Telomerase reverse transcriptase-dependent telomere equilibration mitigates tissue dysfunction in mTert heterozygotes. Dis Model Mech 2, 620-626.
40. Montpetit, A. J., Alhareeri, A. A., Montpetit, M., Starkweather, A. R., Elmore, L. W., Filler, K., Mohanraj, L., Burton, C. W., Menzies, V. S., Lyon, D. E., et al. (2014). Telomere length: a review of methods for measurement. Nurs Res 63, 289-299.
41. Nussey, D. H., Baird, D., Barrett, E., Boner, W., Fairlie, J., Gemmell, N., Hartmann, N., Horn, T., Haussmann, M., Olsson, M., et al. (2014). Measuring telomere length and telomere dynamics in evolutionary biology and ecology. Methods Ecol Evol 5, 299-310.
42. Olovnikov, A. M. (1973). A theory of marginotomy. The incomplete copying of template margin in enzymic synthesis of polynucleotides and biological significance of the phenomenon. Journal of theoretical biology 41, 181-190.
43. Opresko, P. L., and Shay, J. W. (2017). Telomere-associated aging disorders. Ageing Res Rev 33, 52-66.
44. Palm, W., and de Lange, T. (2008). How shelterin protects mammalian telomeres. Annu Rev Genet 42, 301-334.
45. Parry, E. M., Alder, J. K., Lee, S. S., Phillips, J. A., 3rd, Loyd, J. E., Duggal, P., and Armanios, M. (2011). Decreased dyskerin levels as a mechanism of telomere shortening in X-linked dyskeratosis congenita. J Med Genet 48, 327-333.
46. Pawelec, G., Akbar, A., Caruso, C., Solana, R., Grubeck-Loebenstein, B., and Wikby, A. (2005). Human immunosenescence: is it infectious? Immunol Rev 205, 257-268.
47. Ramirez, M. J., and Surralles, J. (2008). Laser confocal microscopy analysis of human interphase nuclei by three-dimensional FISH reveals dynamic perinucleolar clustering of telomeres. Cytogenet Genome Res 122, 237-242.
48. Ruiz-Herrera, A., Nergadze, S. G., Santagostino, M., and Giulotto, E. (2008). Telomeric repeats far from the ends: mechanisms of origin and role in evolution. Cytogenet Genome Res 122, 219-228.
49. Salvador, L., Singaravelu, G., Harley, C. B., Flom, P., Suram, A., and Raffaele, J. M. (2016). A Natural Product Telomerase Activator Lengthens Telomeres in Humans: A Randomized, Double Blind, and Placebo Controlled Study. Rejuvenation Res 19, 478-484.
50. Samani, N. J., Boultby, R., Butler, R., Thompson, J. R., and Goodall, A. H. (2001). Telomere shortening in atherosclerosis. Lancet 358, 472-473.
51. Sampson, M. J., Winterbone, M. S., Hughes, J. C., Dozio, N., and Hughes, D. A. (2006). Monocyte telomere shortening and oxidative DNA damage in type 2 diabetes. Diabetes Care 29, 283-289.
52. Shay, J. W. (2016). Role of Telomeres and Telomerase in Aging and Cancer. Cancer Discov 6, 584-593.
53. Stuart, B. D., Choi, J., Zaidi, S., Xing, C., Holohan, B., Chen, R., Choi, M., Dharwadkar, P., Torres, F., Girod, C. E., et al. (2015). Exome sequencing links mutations in PARN and RTEL1 with familial pulmonary fibrosis and telomere shortening. Nature genetics 47, 512-517.
54. Theodoris, C. V., Mourkioti, F., Huang, Y., Ranade, S. S., Liu, L., Blau, H. M., and Srivastava, D. (2017). Long telomeres protect against age-dependent cardiac disease caused by NOTCH1 haploinsufficiency. The Journal of clinical investigation.
55. Tsakiri, K. D., Cronkhite, J. T., Kuan, P. J., Xing, C., Raghu, G., Weissler, J. C., Rosenblatt, R. L., Shay, J. W., and Garcia, C. K. (2007). Adult-onset pulmonary fibrosis caused by mutations in telomerase. Proceedings of the National Academy of Sciences of the United States of America 104, 7552-7557.
56. Vallejo, A. N., Weyand, C. M., and Goronzy, J. J. (2004). T-cell senescence: a culprit of immune abnormalities in chronic inflammation and persistent infection. Trends Mol Med 10, 119-124.
57. Vera, E., and Blasco, M. A. (2012). Beyond average: potential for measurement of short telomeres. Aging (Albany N. Y.) 4, 379-392.
58. Vera, E., Bernardes de Jesus, B., Foronda, M., Flores, J. M., and Blasco, M. A. (2012). The rate of increase of short telomeres predicts longevity in mammals. Cell Rep 2, 732-737.
59. von Zglinicki, T., Saretzki, G., Ladhoff, J., d'Adda di Fagagna, F., and Jackson, S. P. (2005). Human cell senescence as a DNA damage response. Mech Ageing Dev 126, 111-117.
60. Watson, J. D. (1972). Origin of concatemeric T7 DNA. Nat New Biol 239, 197-201.
61. Weng, N. P., Akbar, A. N., and Goronzy, J. (2009). CD28(−) T cells: their role in the age-associated decline of immune function. Trends Immunol 30, 306-312.
62. Wiemann, S. U., Satyanarayana, A., Tsahuridu, M., Tillmann, H. L., Zender, L., Klempnauer, J., Flemming, P., Franco, S., Blasco, M. A., Manns, M. P., et al. (2002). Hepatocyte telomere shortening and senescence are general markers of human liver cirrhosis. FASEB J 16, 935-942.
63. Wieser, M., Stadler, G., Bohm, E., Borth, N., Katinger, H., Grillari, J., and Voglauer, R. (2006). Nuclear flow FISH: isolation of cell nuclei improves the determination of telomere lengths. Exp Gerontol 41, 230-235.
64. Zou, Y., Sfeir, A., Gryaznov, S. M., Shay, J. W., and Wright, W. E. (2004). Does a sentinel or a subset of short telomeres determine replicative senescence? Mol Biol Cell 15, 3709-3718.

What is claimed is:

1. A method of determining the length of one or more telomere(s) in a collection of genomic DNA molecules comprising telomeres, comprising the steps of:

providing a collection of genomic DNA molecules comprising telomeres having a G-rich strand and a C-rich strand, wherein the genomic DNA molecules comprise sub-telomeric sequences that are adjacent to the telomeres and comprise genomic sequences that are adjacent to the sub-telomeric sequences;

ligating an oligonucleotide to the 5'-end of the C-rich strand, wherein the oligonucleotide comprises a C-rich region complementary to the G-rich strand, and wherein the oligonucleotide comprises a first unique sequence that is 5' to the C-rich region and that is not complementary to the G-rich strand;

digesting the sub-telomeric and genomic sequences with one or more restriction enzymes to produce fragments with overhangs, wherein the fragments comprise genomic sequences or comprise both sub-telomeric and telomeric sequences;

dephosphorylating the 5' ends of the fragments;

ligating adapters to the digested ends of the fragments, wherein each adapter has two strands with complementary regions, wherein a first strand comprises a 5' phosphorylated overhang and a 3' overhang comprising a second unique sequence, and a second strand that is shorter than the first strand and comprises a means for blocking ligation at its 3' end; and non-linearly amplifying the telomeres using a first primer that is identical to the first unique sequence in the oligonucleotide and a second primer that binds to the second unique sequence in the adapter, to produce amplified telomeres; and determining the length of the amplified telomeres.

2. The method of claim 1, wherein the genomic DNA is mammalian DNA.

3. The method of claim 2, wherein the mammalian DNA is human DNA.

4. The method of claim 1, wherein the one or more restriction enzymes produce TA and AT overhangs.

5. The method of claim 1, wherein the one or more restriction enzymes comprise one or more of BfaI, CviAII, MseI, and NdeI.

6. The method of claim 1, wherein the first unique sequence is between 20 and 25 nucleotides in length.

7. The method of claim 1, wherein the second unique sequence is between 30 and 36 nucleotides in length.

8. The method of claim 1, wherein the complementary regions of the adapter are between 18 and 24 nucleotides in length.

9. The method of claim 1, wherein the primer that binds to the first unique sequence in the oligonucleotide is between 18 and 22 nucleotides in length.

10. The method of claim 1, wherein the primer that binds to the second unique sequence in the adapter is between 18 and 22 nucleotides in length.

11. The method of claim 1, wherein the means for blocking ligation at the 3' end of the second strand is a C3 spacer or a dideoxynucleotide.

12. The method of claim 1, wherein the amplifying is by polymerase chain reaction.

13. The method of claim 1, wherein the genomic DNA is from a diseased cell, is from a non-diseased cell, is from a stem cell, is from a cancer cell, is from one or more cells in a benign lesion, or is from an immune cell.

14. The method of claim 13, wherein the immune cell is a peripheral blood mononuclear cell, T cell, NK cell, NKT cell, or mixture thereof.

15. The method of claim 14, wherein the T cell, NK cell, or NKT cell comprises an engineered receptor.

16. The method of claim 15, wherein the engineered receptor is a chimeric antigen receptor.

17. The method of claim 1, wherein the genomic DNA is from an individual that has a medical condition, is suspected of having a medical condition, or is at risk of having a medical condition.

18. The method of claim 17, wherein the medical condition is a genetic disease.

19. The method of claim 17, wherein the medical condition is cancer, atherosclerosis, cardiovascular disease, diabetes, mellitus, or liver cirrhosis.

20. The method of claim 17, wherein the medical condition is a telomeropathy.

21. The method of claim 20, wherein the telomeropathy is idiopathic pulmonary fibrosis, interstitial lung disease, Dyskeratosis congenital, aplastic anemia, cryptic liver disease, Revesz syndrome, Coats Plus syndrome, or Hoyeraal-Hreidersson syndrome.

22. The method of claim 1, wherein the length and abundance of the amplified telomeres are identified.

23. The method of claim 1, wherein the amplified telomeres are quantified.

24. The method of claim 23, wherein the amplified telomeres are quantified by Droplet Digital polymerase chain reaction (DDPCR), Southern blot, or both.

25. The method of claim 1, wherein determination of the length of the telomeres provides a diagnosis and/or prognosis for an individual that has a medical condition, is suspected of having a medical condition, or is at risk of having a medical condition.

26. The method of claim 1, wherein the collection of genomic DNA molecules is from cells that are to be used for therapy.

27. The method of claim 1, wherein the collection of genomic DNA molecules is from cells from an individual at different ages.

28. The method of claim 27, wherein the different ages of the individual are separated by one or more years or are separated by one or more decades.

29. The method of claim 1, wherein the length of the shortest telomere in the collection of genomic DNA molecules is determined.

30. The method of claim 1, wherein the oligonucleotide lacks a 5' phosphoryl group.

* * * * *

SEQUENCE LISTING

<160> NUMBER OF SEQ ID NOS: 11

<210> SEQ ID NO 1
<211> LENGTH: 29
<212> TYPE: DNA
<213> ORGANISM: Artificial Sequence
<220> FEATURE:
<223> OTHER INFORMATION: Synthetic Primer

<400> SEQUENCE: 1
actggccacg tgttttgatc gaccctaac                                29

<210> SEQ ID NO 2
<211> LENGTH: 29
<212> TYPE: DNA
<213> ORGANISM: Artificial Sequence
<220> FEATURE:
<223> OTHER INFORMATION: Synthetic Primer

<400> SEQUENCE: 2
actggccacg tgttttgatc gataaccct                                29

<210> SEQ ID NO 3
<211> LENGTH: 29
<212> TYPE: DNA
<213> ORGANISM: Artificial Sequence
<220> FEATURE:
<223> OTHER INFORMATION: Synthetic Primer

<400> SEQUENCE: 3
actggccacg tgttttgatc gacctaacc                                29

<210> SEQ ID NO 4
<211> LENGTH: 29
<212> TYPE: DNA
<213> ORGANISM: Artificial Sequence
<220> FEATURE:
<223> OTHER INFORMATION: Synthetic Primer

<400> SEQUENCE: 4
actggccacg tgttttgatc gactaaccc                                29

<210> SEQ ID NO 5
<211> LENGTH: 29
<212> TYPE: DNA
<213> ORGANISM: Artificial Sequence
<220> FEATURE:
<223> OTHER INFORMATION: Synthetic Primer

<400> SEQUENCE: 5
actggccacg tgttttgatc gaaaccctaa                               29

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer

<400> SEQUENCE: 6
actggccacg tgttttgatc gaaccctaa                                29

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Primer
<220> FEATURE:
<221> NAME/KEY: misc_feature
<222> LOCATION: (20)..(20)
<223> OTHER INFORMATION: C3 spacer

<400> SEQUENCE: 7
ggttactttg taagcctgtc                                                  20

<210> SEQ ID NO 8
<211> LENGTH: 56
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (56)..(56)
<223> OTHER INFORMATION: C3 spacer

<400> SEQUENCE: 8
tagacaggct tacaaagtaa ccatggtgga gaattctgtc gtcttcacgc tacatt         56

<210> SEQ ID NO 9
<211> LENGTH: 56
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (56)..(56)
<223> OTHER INFORMATION: C3 spacer

<400> SEQUENCE: 9
atgacaggct tacaaagtaa ccatggtgga gaattctgtc gtcttcacgc tacatt         56

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
tgtagcgtga agacgacaga a                                               21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tggccacgtg ttttgatcga                                                  20
```